United States Patent
Ito et al.

(10) Patent No.: US 11,479,511 B2
(45) Date of Patent: Oct. 25, 2022

(54) ZIRCONIA SINTERED BODY AND PRODUCTION METHOD THEREOF

(71) Applicant: TOSOH CORPORATION, Yamaguchi (JP)

(72) Inventors: Akiko Ito, Yamaguchi (JP); Ayako Watanabe, Yamaguchi (JP); Sho Azechi, Yamaguchi (JP); Hitoshi Nagayama, Yamaguchi (JP); Hiroyuki Fujisaki, Yamaguchi (JP)

(73) Assignee: TOSOH CORPORATION, Yamaguchi (JP)

( * ) Notice: Subject to any disclaimer, the term of this patent is extended or adjusted under 35 U.S.C. 154(b) by 0 days.

(21) Appl. No.: 17/038,646

(22) Filed: Sep. 30, 2020

(65) Prior Publication Data

US 2021/0101838 A1  Apr. 8, 2021

(30) Foreign Application Priority Data

Oct. 8, 2019 (JP) .............................. JP2019-185075

(51) Int. Cl.
  *C04B 35/488* (2006.01)
  *C04B 35/645* (2006.01)

(52) U.S. Cl.
  CPC ........ *C04B 35/4885* (2013.01); *C04B 35/645* (2013.01); *C04B 2235/3217* (2013.01); *C04B 2235/3246* (2013.01); *C04B 2235/762* (2013.01); *C04B 2235/765* (2013.01); *C04B 2235/785* (2013.01); *C04B 2235/786* (2013.01)

(58) Field of Classification Search
  CPC .. C04B 35/486; C04B 35/488; C04B 35/4885
  See application file for complete search history.

(56) References Cited

U.S. PATENT DOCUMENTS

| | | | | |
|---|---|---|---|---|
| 11,021,401 | B2 * | 6/2021 | Kawamura | ........... C04B 35/486 |
| 2016/0310245 | A1 | 10/2016 | Fujisaki et al. | |
| 2018/0235847 | A1 | 8/2018 | Balasubramanian et al. | |
| 2020/0223756 | A1 * | 7/2020 | Kawamura | ............. C04B 35/64 |
| 2021/0246075 | A1 * | 8/2021 | Kawamura | ........... C04B 35/486 |

FOREIGN PATENT DOCUMENTS

| | | | |
|---|---|---|---|
| EP | 3 088 373 | A1 | 11/2016 |
| JP | 2008-222450 | A | 9/2008 |
| JP | 2011-73907 | A | 4/2011 |
| JP | 2015-143178 | A | 8/2015 |
| JP | 2018-52806 | A | 4/2018 |
| WO | WO-2019180766 | A1 * | 9/2019 ............... A61K 6/16 |

OTHER PUBLICATIONS

Extended European Search Report in the corresponding European patent application No. 20199626.1 dated Mar. 4, 2021.

* cited by examiner

*Primary Examiner* — Karl E Group
(74) *Attorney, Agent, or Firm* — Greenblum & Bernstein, P.L.C.

(57) ABSTRACT

A zirconia sintered body is provided and includes yttria and zirconia, containing yttria by a content ranging from 4.5 mol % or more to 6.5 mol % or less and zirconia as the remainder, the total light transmittance of a 1-mm thick sample measured in compliance with JIS K 7361-1 being 46.5% or higher, the three-point bending strength being 700 MPa or higher, and a ratio of an integrated value for the total light transmittance to an integrated value for the parallel light transmittance of a 1-mm thick sample measured at the measurement wavelength ranging from 400 to 700 nm being 1.3% or less.

9 Claims, 1 Drawing Sheet

[Figure 1]
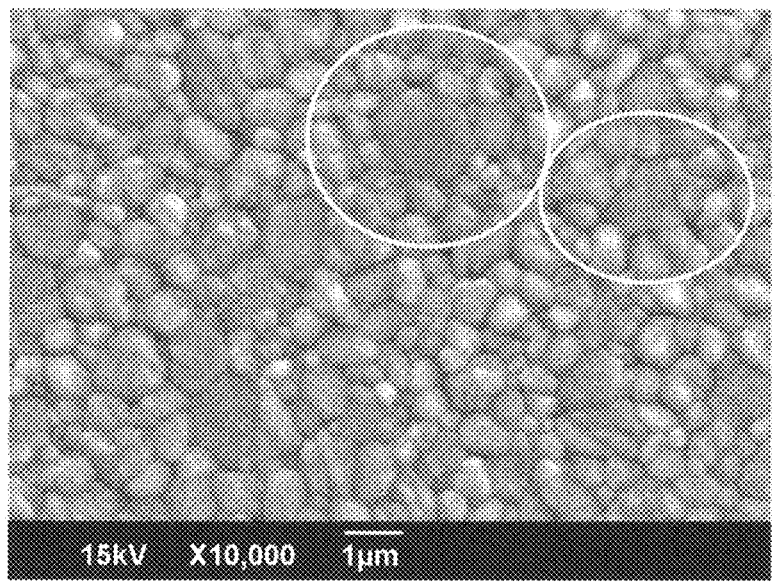
[Figure 2]
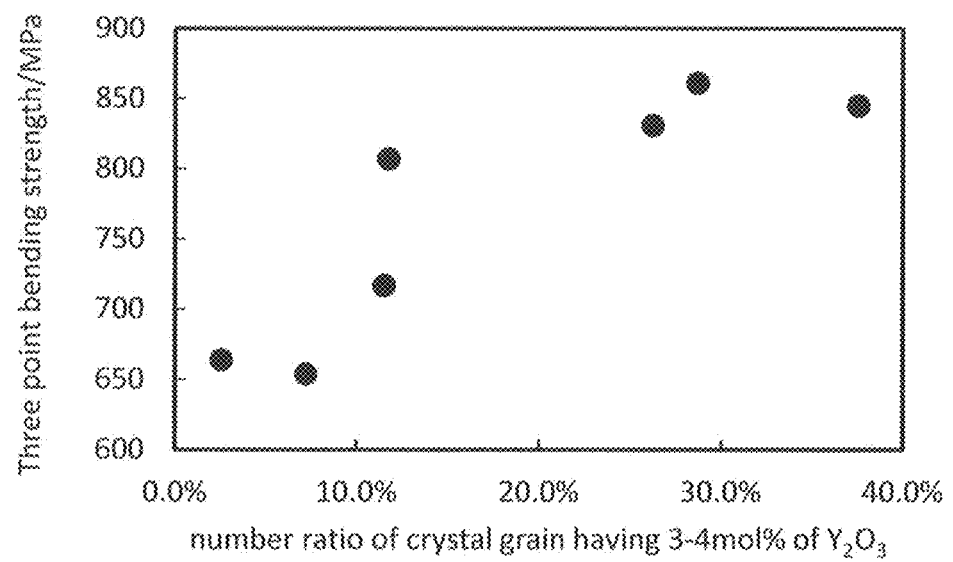

ZIRCONIA SINTERED BODY AND PRODUCTION METHOD THEREOF

TECHNICAL FIELD

Zirconia sintered bodies applied for use as dental prosthetic materials such as crowns and bridges are desired to have translucency equal to that of natural teeth. To meet such a desire, it has been examined to improve the translucency of a zirconia sintered body by increasing the content of the stabilizer (Patent Literature 1). If the content of the stabilizer is increased, the translucency of the zirconia sintered body will improve while the mechanical strength of the sintered body will decrease. Therefore, it is difficult to apply the zirconia sintered body disclosed in Patent Literature 1 and the like as a dental prosthetic material especially desired to have a sufficiently high mechanical strength.

Patent Literature 2 discusses an improvement of the mechanical strength of a zirconia sintered body with a high content of the stabilizer, and discloses a zirconia sintered body capable of satisfying the mechanical strength desired for use in dental prosthetic materials especially desired to have a sufficiently high mechanical strength, even when the sintered body contains a stabilizer by a content at which the mechanical strength of the sintered body may degrade. In addition, Patent Literature 3 discloses a zirconia sintered body similarly capable of satisfying the mechanical strength desired for use in most dental prosthetic materials, which contains a stabilizer in a range of 5 mol % or more, a range of content in which the mechanical strength may considerably degrade, which is implemented by controlling the sintering atmosphere.

CITATION LIST

Patent Literature

[Patent Literature 1]
  JP 2015-143178 A
[Patent Literature 2]
  JP 2018-052806 A
[Patent Literature 3]
  JP 2011-073907 A

SUMMARY OF INVENTION

Technical Problem

In producing dental prosthetic materials, a sintering furnace that performs sintering in an air atmosphere under atmospheric pressure has been generally used. Therefore, it is difficult to use a zirconia sintered body produced by sintering that requires equipment for hot isostatic pressing (HIP), microwave sintering, and the like and sintering that requires control of the atmosphere such as oxygen atmosphere as a zirconia sintered body applied to dental prosthetic materials.

The present disclosure is intended to provide at least one of a zirconia sintered body which can be produced even by using a sintering furnace that performs sintering in an air atmosphere with the mechanical strength and the translucency desired for use in dental prosthetic materials, a production method thereof, a precursor thereto, and a preparation method of the precursor.

Solution to Problem

For the present disclosure, considering that sintering in an air atmosphere under atmospheric pressure has been generally used in producing dental prosthetic materials, the inventor has examined means for obtaining a zirconia sintered body containing a high content of yttria with a sufficiently high mechanical strength and translucency. As a result, the inventor has invented a zirconia sintered body containing a high content of the stabilizer with the translucency not too high and an improved mechanical strength achieved even with the translucency suitable for dental prosthetic materials.

That is, the present invention includes inventions as claimed in Claims, and the gist of the present disclosure is as follows.

[1] A zirconia sintered body comprising yttria and zirconia, containing yttria in a content ranging from 4.5 mol % or more to 6.5 mol % or less and zirconia as the remainder, the total light transmittance of a 1-mm thick sample measured in compliance with JIS K 7361-1 being 46.5% or higher, the three-point bending strength being 700 MPa or higher, and a ratio of an integrated value for total light transmittance to an integrated value for parallel light transmittance of a 1-mm thick sample measured at measurement wavelength ranging from 400 to 700 nm being 1.3% or less.

[2] The zirconia sintered body according to Item [1], which contains alumina.

[3] The zirconia sintered body according to Item [1] or [2], wherein the content of alumina is 0.005% by mass or higher and 0.2% by mass or less.

[4] The zirconia sintered body according to any one of Items [1] to [3], wherein an average crystal grain size is in a range of 0.5 µm or greater and 1.8 µm or less.

[5] The zirconia sintered body according to any one of Items [1] to [4], containing crystal grains with different yttria concentrations.

[6] The zirconia sintered body according to any one of Items [1] to [5], wherein a difference in the yttria concentration between the crystal grain with the highest yttria concentration and the crystal grain with the lowest yttria concentration is 2.7 mol % or higher and 7 mol % or less.

[7] The zirconia sintered body according to any one of Items [1] to [6], wherein a number ratio of crystal grains with the yttria concentration ranging from 3.0 mol % or higher to 4.0 mol % or less to all the crystal grains is 10% or higher and 50% or less.

[8] A production method of the zirconia sintered body according to any one of Items [1] to [7], the production method including a process of sintering a green body including a zirconia powder which includes a yttria source and zirconia, wherein the content of the yttria source is 4.5 mol % or more and 6.5 mol % or less and the remainder is zirconia, a total ratio of tetragonal and cubic crystals to the entire crystal phase of zirconia is 90% or less, a Brunauer, Emmett and Teller (BET) specific surface area is 7.5 $m^2$/g or more and 15 $m^2$/g or less, and an average crystallite size is 325 Å or greater.

[9] The production method according to Item [8], wherein the zirconia powder includes zirconia powder particles of different yttria contents.

[10] The production method according to Item [9], wherein a difference between the yttria content of one zirconia powder particle and the yttria content of the other zirconia powder particle is greater than 3.0 mol %.

[11] The production method according to Item [9] or [10], wherein the sintering in the process is normal pressure sintering.

[12] A zirconia powder including a yttria source and zirconia, wherein the content of the yttria source is 4.5 mol % or more and 6.5 mol % or less and the remainder is zirconia, a total ratio of tetragonal and cubic crystals to the entire crystal phase of zirconia is 90% or less, a BET specific surface area is 7.5 m²/g or more and 15 m²/g or less, and an average crystallite size is 325 Å or greater.

[13] A production method of a pre-sintered body, wherein the zirconia powder according to Item [12] is used.

Advantageous Effects of Invention

The present disclosure is capable of providing at least one of a zirconia sintered body which can be produced even by using a sintering furnace that performs sintering in an air atmosphere with the mechanical strength and the translucency desired for use in dental prosthetic materials, a production method thereof, a precursor thereto, and a preparation method of the precursor.

BRIEF DESCRIPTION OF DRAWINGS

FIG. 1 is a scanning electron microscopy (SEM) observation view of a surface of a zirconia sintered body of Example 1.

FIG. 2 is a graph illustrating a relationship between the number ratio of crystal grains with the yttria concentration ranging from 3 to 4 mol % to the entire zirconia sintered body and the three-point bending strength.

DESCRIPTION OF EMBODIMENTS

Now, an embodiment of the zirconia sintered body according to the present disclosure will be described below.

The zirconia sintered body of the present embodiment is a zirconia sintered body comprising yttria and zirconia, containing yttria by a content ranging from 4.5 mol % or more to 6.5 mol % or less and zirconia as the remainder, in which the total light transmittance of a 1-mm thick sample measured in compliance with JIS K 7361-1 is 46.5% or higher, the three-point bending strength is 700 MPa or higher, and a ratio of an integrated value for the total light transmittance to an integrated value for the parallel light transmittance of a 1-mm thick sample measured at the measurement wavelength ranging from 400 to 700 nm is 1.3% or less.

In the present embodiment, a "zirconia sintered body" refers to a sintered body including zirconia as its main phase, in which the ratio of zirconia ($ZrO_2$) to the entire composition of the sintered body is the highest of all the ingredients. In the zirconia sintered body, the mass ratio of zirconia ($ZrO_2$) to the mass of the zirconia sintered body may be 95% by mass or more and 100% by mass or less, may further be 99% by mass or less, and may yet further be 99.5% by mass or more and 100% by mass or less.

The zirconia sintered body of the present embodiment comprises yttria and zirconia. Yttria ($Y_2O_3$) functions as a stabilizer without coloring zirconia. Therefore, the zirconia sintered body according to the present embodiment can be regarded as a yttria-containing zirconia sintered body, a yttria solid solution zirconia sintered body, a yttria-stabilized zirconia sintered body, a yttria partially stabilized zirconia sintered body, or a partially stabilized zirconia sintered body. It is preferable if the zirconia sintered body of the present embodiment comprises yttria and zirconia as yttria-containing zirconia. In addition, it is more preferable if at least a part of the yttria is dissolved in zirconia in solid and further contains no yttria that is not dissolved in zirconia in solid.

In the present embodiment, the term "contains no yttria that is not dissolved . . . in solid" refers to a state in which no x-ray diffractometry (XRD) peak coming from yttria ($Y_2O_3$) is observed in the XRD measurement and an analysis of XRD patterns described below, and it is permissible if yttria is included in a content not affecting the characteristics of the zirconia sintered body according to the present embodiment.

The yttria content is 4.5 mol % or higher and 6.5 mol % or less, and preferably higher than 4.5 mol % and 6.0 mol % or less, 4.7 mol % or higher and 5.8 mol % or less, 4.8 mol % or higher and 5.5 mol % or less, or 5.0 mol % or higher and 5.5 mol % or less. In another embodiment, the yttria content is 4.5 mol % or higher, higher than 4.5 mol %, 4.7 mol % or higher, 4.8 mol % or higher, or 5.0 mol % or higher, or 6.5 mol % or less, 6.0 mol % or less, 5.8 mol % or less, or 5.5 mol % or less. If the yttria content is less than 4.5 mol %, it becomes difficult to stably obtain a zirconia sintered body with a high translucency. On the contrary, if the yttria content is higher than 6.5 mol %, the mechanical strength may degrade. For easier obtainment of a zirconia sintered body with a high translucency in repetitive production with a high reproducibility, it is preferable if the yttria content is 5.0 mol % or higher and 6.0 mol % or less, 5.0 mol % or higher and 5.8 mol % or less, or 5.2 mol % or higher and 5.6 mol % or less.

The content of yttria in the zirconia sintered body according to the present embodiment is expressed by the molar ratio (mol %) of yttria ($Y_2O_3$) to the total content of zirconia ($ZrO_2$) and yttria ($Y_2O_3$) in the zirconia sintered body, which is calculated by the following expression: $\{Y_2O_3 \text{ [mol]}/(ZrO_2+Y_2O_3) \text{ [mol]}\} \times 100$.

The zirconia sintered body of the present embodiment may contain alumina ($Al_2O_3$) and may include zirconia, yttria, and alumina. The alumina content is 0% by mass or higher and 0.2% by mass or less, 0% by mass or higher and 0.15% by mass or less, or 0% by mass or higher and 0.1% by mass or less, for example. The sintering will more easily advance if a small amount of alumina is included; so the alumina content is 0% by mass or higher and 0.2% by mass or less, 0.005% by mass or higher and 0.15% by mass or less, 0.01% by mass or higher and 0.12% by mass or less, 0.015% by mass or higher and 0.1% by mass or less, or 0.02% by mass or higher and 0.07% by mass or less, for example.

The alumina content in the zirconia sintered body of the present embodiment refers to the mass ratio (% by mass) of alumina to the total of zirconia ($ZrO_2$), yttria ($Y_2O_3$), ad alumina ($Al_2O_3$) in the zirconia sintered body, which is expressed by the following expression: $\{Al_2O_3 \text{ [g]}/(ZrO_2+Y_2O_3+Al_2O_3)[g]\} \times 100$.

An element with a function for coloring zirconia (hereinafter also referred to as "colorant") may be included within an extent not impairing the effect of the zirconia sintered body of the present embodiment. The colorant is an element having a function for coloring zirconia, and may be an element having a function for preventing phase transition of zirconia. Specific examples of the colorant include at least one of transition metal elements and lanthanoid rare earth elements; preferable examples of the colorant include one or more selected from the group consisting of iron (Fe), cobalt (Co), nickel (Ni), manganese (Mn), praseodymium (Pr), neodymium (Nd), europium (Eu), gadolinium (Gd), terbium (Tb), erbium (Er), and ytterbium (Yb); more preferable examples of the colorant include one or more selected from the group consisting of iron, cobalt, manganese, praseodymium, neodymium, terbium, and erbium; and yet more preferable examples include one or more selected from the group consisting of iron, cobalt and erbium.

The zirconia sintered body of the present embodiment may include inevitable impurities such as hafnia ($HfO_2$). The content of hafnia as the inevitable impurity may be 2.0% by mass or less, for example. However, it is preferable if no element greatly affecting the effect of the zirconia sintered body of the present embodiment be included. Specifically, for example, it is preferable if the zirconia sintered body of the present embodiment satisfy at least one of the following conditions: the content of magnesium expressed in terms of magnesia (MgO) is 0 ppm by mass or higher and 500 ppm by mass or less; the content of silicon expressed in terms of silica ($SiO_2$) is 0 ppm by mass or higher and 500 ppm by mass or less; and the content of titanium expressed in terms of titania ($TiO_2$) is 0 ppm by mass or higher and 500 ppm by mass or less, and it is preferable if the content of magnesium, silicon, and titan be 0 ppm by mass or higher and 500 ppm by mass or less.

The composition of the zirconia sintered body of the present embodiment can be determined by a general composition analysis (for example, intracranial pressure (ICP) monitoring). In another embodiment, if the production method of the resulting sintered body is already known, the composition of the zirconia sintered body can be determined based on the composition of the raw materials used.

The zirconia sintered body of the present embodiment preferably at least includes either one of tetragonal and cubic crystals in its crystal phase, and more preferably includes tetragonal and cubic crystals. The zirconia sintered body of the present embodiment preferably includes either of tetragonal and cubic crystals in the crystal phase as its main phase; and it is preferable if the total ratio of the tetragonal and the cubic crystals to the crystal phase (hereinafter also referred to as "tetragonal+cubic crystal ratio") be 95% or higher or 99% or higher. In the present embodiment, the crystal phase other than the tetragonal and the cubic crystals included in the crystal phase can be considered as a monoclinic crystal. The ratio of the monoclinic crystal to the entire crystal phase (hereinafter also referred to as "monoclinic crystal ratio") is 0% or higher or 0.5% or higher and less than 5%, preferably less than 1%.

The tetragonal+cubic crystal ratio and the monoclinic crystal ratio are values calculated by the following expressions from the powder X-ray diffraction (hereinafter also referred to as "XRD") patterns on the surface of the zirconia sintered body of the present embodiment.

$$f_{T+C}=[I_t(111)+I_c(111)]/[I_m(111)+I_m(11\text{-}1)+I_t(111)+I_c(111)]$$

$$f_M=1-f_{T+C}$$

In the above expressions, $f_{T+C}$ is the tetragonal+cubic crystal ratio, $f_M$ is the monoclinic crystal ratio, $I_t(111)$ is the integrated intensity of the tetragonal face (111), $I_c(111)$ is the integrated intensity of the monoclinic crystal face (111), $I_m(111)$ is the integrated intensity of the monoclinic crystal face (111), and $I_m(11\text{-}1)$ is the integrated intensity of the monoclinic crystal (11-1).

The integrated intensity of each crystal face can be calculated by profile-fitting on the XRD pattern after smoothing and background elimination using divided pseudo-Voigt function. The analysis on the XRD patterns such as the smoothing, background elimination, and calculation of the integrated intensity can be performed by using an analyzer program attached to the X-ray diffraction apparatus (e.g., PDXL: Integrated X-ray powder diffraction software Ver. 2.2, a product of Rigaku Corporation) and the like.

It is preferable if the XRD pattern on the surface of the zirconia sintered body of the present embodiment be obtained by XRD measurement under the following conditions.

Radiation source: CuKα ray (λ=0.15418 nm):
Measurement mode: Continuous scanning
Scan speed: 4°/min
Step width: 0.02°
Measurement range: 2θ=26° to 33°

The XRD measurement can be performed by using a common X-ray diffraction apparatus (e.g., MiniFlex of Rigaku Corporation).

Examples of the XRD peak equivalent to each crystal faces of zirconia measured by the XRD measurement described above includes XRD peaks having the peak top in the term 2θ in the following expressions.

XRD peak equivalent to the monoclinic crystal face (111): 2θ=31±0.5°

XRD peak equivalent to the monoclinic crystal face (11-1): 2θ=28±0.5°

XRD peak equivalent to the tetragonal face (111): 2θ=30±0.5°

XRD peak equivalent to the cubic crystal face (111): 2θ=30±0.5°

The XRD peak equivalent to the tetragonal face (111) and the XRD peak equivalent to the cubic crystal face (111) are measured as one overlapped peak. Accordingly, the term $I_t(111)+I_c(111)$ in the above expression may be calculated based on the integrated intensity of one XRD peak having its peak top at 2θ=30±0.5°.

It is preferable if the relative density of the zirconia sintered body of the present embodiment be 99.8% or higher or 99.85% or higher. The relative density is 100% or less, and further preferably, it is 99.98% or less.

The term "relative density" in the present embodiment refers to the ratio (%) of the measured density to the theoretical density. The measured density is the ratio ($g/cm^3$) of the volume measured by the Archimedes method to the mass measured by mass measurement. The theoretical density (the theoretical density used in the present embodiment) is a density ($g/cm^3$) calculated by the following expressions (1) to (4).

$$A=0.5080+0.06980X/(100+X) \quad (1)$$

$$C=0.5195-0.06180X/(100+X) \quad (2)$$

$$p_Z=[124.25(100-X)+225.81X]/[150.5(100+X)A^2C] \quad (3)$$

$$p_0=100/[(Y/3.987)+(100-Y)/p_Z] \quad (4)$$

In the expressions (1) to (4), $p_0$ is the theoretical density, $p_Z$ is the theoretical density of zirconia, A and C are the constant, respectively, X is the molar ratio (mol %) of yttria to the total of zirconia ($ZrO_2$) and yttria ($Y_2O_3$), and Y is the mass ratio of alumina (% by mass) to the total of zirconia, yttria, and alumina in the zirconia sintered body.

Note that if the zirconia sintered body of the present embodiment includes metal oxides and rare earth oxides other than zirconia, yttria, and alumina, the terms "Y" and "Y/3.987)" in the above expression (4) may be substituted as follows.

$$Y=Y_1+Y_2+\ldots Y_n$$

$$(Y/3.987)=(Y_1/W_1+Y_2/W_2+\ldots Y_n/W_n)$$

where $Y_1, Y_2, \ldots, Y_n$ are mass ratios (% by mass) of the metal oxides or the rare earth oxides other than zirconia and yttria, $W_1, W_2, \ldots, W_n$ are the density ($g/cm^3$) of the metal oxides or the rare earth oxides other than zirconia and yttria. Note that because inevitable impurities are considered for the values obtained by using the expressions (1) to (4), the expression (4) may not be substituted for hafnia of the inevitable impurities.

In the zirconia sintered body of the present embodiment, the average crystal grain size is 0.5 µm or greater and 1.8 µm or less or 0.55 µm or greater and 1.6 µm or less. For zirconia sintered bodies, the mechanical strength tends to be higher as the average crystal grain size is smaller, while in the zirconia sintered body of the present embodiment, a high mechanical strength can be easily achieved even if the average crystal grain size is 0.5 µm or greater in the range of the yttria content. It is preferable if the average crystal grain size be 0.5 µm or greater and 1 µm or less, 0.55 µm or greater and 0.8 µm or less, 0.6 µm or greater and less than 0.8 µm, or 0.7 µm or greater and less than 0.8 µm.

The average crystal grain size in the present embodiment can be calculated by a planimetric method which uses SEM observation views. Specifically, the average crystal grain size can be calculated by using the following expression after drawing a circle with a known area on the SEM observation view, measuring the number of the crystal grains (Nc) within the circle and the number of the crystal grains (Ni) on the circumference of the circle, and obtaining 250±50 crystal grains as the total number of the crystal grains (Nc+Ni).

$$\text{Average crystal grain size} = 2/[\pi \times \{(Nc+(\frac{1}{2}) \times Ni)/(A/M^2)\}]^{0.5}$$

In the above expression, Nc is the number of the crystal grains within the circle, Ni is the number of the crystal grains on the circumference of the circle, A is the area of the circle, and M is the power of magnification by the observation using the scanning electron microscope (e.g., the magnification powers ranging from 5,000 to 10,000). Note that if the number of the crystal grains in one SEM observation view is less than 200, the total number of the crystal grains (Nc+Ni) may be adjusted to 250±50 grains using multiple SEM observation views.

For the zirconia sintered body to be used for the SEM observation, a zirconia sintered body with the surface roughness Ra≤0.02 µm processed by thermal etching (at 1,400° C. to 1,500° C. in an air atmosphere, for example) may be used.

The zirconia sintered body of the present embodiment may include crystal grains of different sizes, preferably include coarse crystal grains and fine crystal grains, and more preferably include a structure in which coarse crystal grains and multiple crystal grains form a grain boundary. Specifically, as illustrated in the portion surrounded with a circle in FIG. 1, examples of the zirconia sintered body of the present embodiment includes a structure in which crystal grains with the longitudinal size (the longest length of a crystal grain) of less than 1.0 µm are distributed so as to surround the outer periphery of crystal grains with the longitudinal size of 1.0 µm or greater.

The zirconia sintered body of the present embodiment preferably includes crystal grains of different yttria concentrations, and more preferably includes crystal grains with different yttria concentrations. A zirconia sintered body generally includes crystal grains with substantially the same yttria concentration. On the contrary, a zirconia sintered body including crystal grains of different yttria concentrations tends to have a characteristic in which the characteristics of the crystal grains are synergistically exhibited.

In the zirconia sintered body of the present embodiment, it is preferable, for example, if the difference in the yttria concentration between the crystal grain with the highest yttria concentration and the crystal grain with the lowest yttria concentration (hereinafter also referred to as the "difference in the concentration among the crystal grains") be 2.7 mol % or higher and 7 mol % or less. Further, the mechanical strength of a zirconia sintered body tends to become higher if the difference in the concentration among the crystal grains is 3 mol % or higher and 7 mol % or less, or yet higher if it is 3.2 mol % or higher and 5 mol % or less.

Because the mechanical strength tends to become high in the range of the yttria content of the present embodiment, it is preferable if the number ratio of the crystal grains with the yttria concentration in the crystal grains of 3.0 mol % or higher and 4.0 mol % or less be 10% or higher and 50% or less. It is more preferable if the number ratio of the crystal grains with the yttria concentration of 3.0 mol % or higher and 4.0 mol % or less be 25% or higher and 40% or less because the mechanical strength tends to be especially high in this range of the number ratio.

In the present embodiment, the yttria concentration of the crystal grains can be calculated by scanning electron microscopy-energy dispersive X-ray spectrometry (SEM-EDS) analysis. Specifically, after determining the crystal grains using SEM observation views obtained by observation at the magnification power that enables observation of the grain boundary between the crystal grains (e.g., at the power of 10,000, preferably at the power at which the number of the crystal grains in the SEM observation view becomes 150±25), the yttria concentration of the crystal grains may be calculated by the following expression for the crystal grains in the SEM observation view that can be respectively observed as a whole grain (i.e., crystal grains other than the crystal grains on the outer periphery of the SEM observation view).

$$C = C_Y / \{C_Y + (2 \times C_{Zr})\} \times 100$$

In the above expression, C is the yttria concentration (mol %) of the crystal grain, $C_Y$ is the total intensity of the energy dispersive X-ray spectroscopy (EDS) spectra of yttrium included in the crystal grains, and $C_{Zr}$ is the total intensity of the EDS spectra of zirconium included in the crystal grains.

The number ratio of the crystal grains with the yttria concentration of 3.0 mol % or higher and 4.0 mol % or less can be calculated from the number ratio of the crystal grains with the yttria concentration of 3.0 mol % or higher and 4.0 mol % or less to the total number of all the crystal grains observed (determined) by the above SEM-EDS analysis.

In the present embodiment, the SEM-EDS analysis can be performed based on measurement performed by using a common SEM-EDS apparatus (e.g., SEM: JSM-7600F, a product of JEOL Ltd., EDS: NSS312E, a product of Thermo Fisher Scientific K.K.). The crystal grains can be determined and the constant volume value can be calculated by using the apparatus described above and the functions installed to the apparatus (analysis programs, and the like) based on the peak intensity of the EDS spectra of respective elements.

In the zirconia sintered body of the present embodiment, the total light transmittance of a 1-mm thick sample measured in compliance with JIS K 7361-1 (the transmittance will be also hereafter referred to as "light transmittance") is 46.5% or higher, and it is preferable if the above total light transmittance is higher than 47%, 47.5% or higher, or 48% or higher. A zirconia sintered body with the light transmittance lower than the above levels is not suitable for application in some dental prosthetic materials such as dental prosthetic materials for front teeth. The zirconia sintered body of the present embodiment with the light transmittance of 48.5% or higher, preferably 49%, is more likely suitable for use as dental prosthetic materials for leading end portions of front teeth, for which especially high translucency is desired. The light transmittance of the zirconia sintered body of the present embodiment with the above range of yttria content is 54% or higher, 53% or higher, or 52% or higher, for example.

In the present embodiment, the light transmittance is the total light transmittance measured by using daytime light as the incident light, which can be measured by using a method compliant with JIS K 7361-1. Additionally, the parallel light transmittance is the parallel light transmittance measured by using daytime light as the incident light, which can be measured by using a method compliant with JIS K 7361-1. Examples of methods of measuring the light transmittance and parallel transmittance include a measurement method which uses a 1-mm thick disk-like zirconia sintered body with the surface roughness Ra≤0.02 μm on both surfaces as the measurement sample and a hazemeter including a D65 light source as the light source (e.g., Hazemeter NDH4000, a product of Nippon Denshoku Industries Co., Ltd.) as the measurement apparatus.

In the zirconia sintered body of the present embodiment, a ratio of an integrated value for the parallel light transmittance to an integrated value for the total light transmittance (hereinafter also referred to as "PT/TT ratio") obtained by measurement on a 1-mm thick sample at the measurement wavelength in the range of 400 to 700 nm is 1.3% or less, and it is preferable if the ratio be 1.2% or less, 1.0% or less, 0.8% or less, or 0.6% or less. The PT/TT ratio is one of the indices for a ratio between the parallel light transmittance and the total light transmittance in the visible light region, and the zirconia sintered body of the present embodiment that satisfies the PT/TT ratio in the above range implements a zirconia sintered body with controlled transparency and sufficient translucency. With this configuration, the zirconia sintered body of the present embodiment is suitable for use in dental prosthetic material, which can be visually recognized as a material with the translucency closer to the translucency of natural teeth. In the zirconia sintered body of the present embodiment, it is preferable if the PT/TT ratio be higher than 0% or 0.3% or higher. Examples of the range of the PT/TT ratio include a range from a level higher than 0% to 1.3% or less, 0.1% or higher and 1.0% or less, or 0.3% or higher and 0.9% or less.

In the present embodiment, the PT/TT ratio can be calculated based on a ratio of the integrated values of the parallel light transmittance and the total light transmittance measured by UV-VIS spectra measurement at each wavelength. Examples of the measurement conditions for UV-VIS spectra measurement include the following conditions.

Measurement method: UV-VIS spectrophotometry
Measurement system: Double-beam system
Light source: Halogen lamp
Range of measurement wavelength: 400 nm-700 nm
Wavelength step: 0.5 nm Measurement of the PT/TT ratio can be implemented by a method which uses a 1-mm thick disk-like zirconia sintered body with the surface roughness Ra≤0.02 μm on both surfaces as the measurement sample and a common UV-VIS spectrophotometer (e.g., Spectrophotometer V-650, a product of JASCO Corporation) as the measurement apparatus, for example.

Because the zirconia sintered body of the present embodiment satisfies the above light transmittance and the above PT/TT ratio, it can be considered as a translucent zirconia sintered body, a highly translucent zirconia sintered body, a light transmissive zirconia sintered body, or the like.

In the zirconia sintered body of the present embodiment, it is preferable if the three-point bending strength be 700 MPa or higher, 715 MPa or higher, 730 MPa or higher, or 780 MPa or higher. With the configuration that satisfies the above three-point bending strength, the zirconia sintered body of the present embodiment can be applied as a dental prosthetic material with smaller dimensions. It is more preferable if the three-point bending strength be 800 MPa or higher or 820 MPa or higher. With the configuration that satisfies the above three-point bending strength as well as the above light transmittance and the above PT/TT ratio, the zirconia sintered body of the present embodiment can be applied as a dental prosthetic material for a bridge of four or more pieces for front teeth. The three-point bending strength is more preferable as it becomes higher. Specifically, if the yttria content in the present embodiment is satisfied, the three-point bending strength is 1,200 MPa or less, 1,000 MPa or less, or 900 MPa or less, for example. The three-point bending strength tends to decrease as the yttria content becomes higher, and thus if the yttria content is 5.0 mol % or higher, the three-point bending strength may be 1,000 MPa or less, for example.

In the present embodiment, the three-point bending strength is a value obtained by a three-point bending test compliant to JIS R 1601. For measurement of the three-point bending strength, a method may be used which uses a column-like sintered body at the distance between support points of 30 mm, width of 4 mm, and thickness of 3 mm as the measurement sample, and an average value obtained from measurement values of 10 times of the measurement may be used as the three-point bending strength of the zirconia sintered body of the present embodiment.

Further, in the zirconia sintered body of the present embodiment, it is preferable if the frequency of the monoclinic crystal in the fracture origin after measurement of the three-point bending strength (hereinafter also simply referred to as "monoclinic crystal frequency") be 40% or higher or 50% or higher, and 80% or less or 75% or less. The monoclinic crystal frequency is a value obtained by the microscopic Raman spectroscopic analysis on optical microscope observation views for a fracture origin generated by the measurement of the three-point bending strength, and is a ratio of the number of the measurement regions in which the monoclinic crystal ratio (Vm) in the microscopic Raman spectroscopic analysis is 1% or higher. Specifically, a 900 μm×600 μm optical microscope observation view is sectioned into a lattice of 20 μm×20 μm measurement regions, the Raman spectra of each measurement region are measured, and the monoclinic crystal ratio (Vm) is calculated by using the following expression.

$$Vm=(a \times P2)/(b \times P1 + a \times P2)$$

In the above expression, Vm is the monoclinic crystal ratio, P1 is the area of a peak having the peak top at $149 \pm 3$ cm$^{-1}$, P2 is the total area of a peak having the peak top at $179 \pm 3$ cm$^{-1}$ and a peak having the peak top at $189 \pm 3$ cm$^{-1}$, and a and b are a coefficient, respectively (a=0.5 and b=2.2).

The monoclinic crystal frequency can be calculated as a ratio of the number of the measurement regions with the monoclinic crystal ratio (Vm) of 1% or higher to the total number of the measurement regions (=1,350).

The microscopic Raman spectroscopy analysis can be performed on values measured by using a common microscopic Raman apparatus (e.g., NRS-5100, a product of JASCO Corporation), and the peak area of the peak in each measurement regions can be calculated by using analysis software attached to the apparatus (e.g., Spectra Manager, a product of JASCO Corporation).

In the zirconia sintered body of the present embodiment, the fracture toughness measured by a method compliant with a single edge precracked beam (SEPB) method prescribed under JIS R 1607 is preferably 5 MPa·m$^{1/2}$ or less, and more preferably 3 MPa·m$^{1/2}$ or higher and 5 MPa·m$^{1/2}$ or less, for example.

The zirconia sintered body of the present embodiment is preferably a sintered body in a state that can be obtained by normal-pressure sintering, i.e., a so-called normal-pressure sintered body, and is more preferably an normal air-pressure sintered body in a state that can be obtained by normal-pressure sintering in an air atmosphere (hereinafter also referred to as "atmospheric sintering"). With this configuration, the present embodiment can be readily manufactured by using a sintering furnace generally used for production of dental prosthetic materials.

The zirconia sintered body of the present embodiment is suitable for use as a dental prosthetic material, among dental materials, further for use as a dental prosthetic material for front teeth, and yet further for use as a dental prosthetic material for a leading edge portion of front teeth. In another embodiment, the zirconia sintered body of the present embodiment can be used as a dental prosthetic material for crowns, bridges, inlays, onlays, and the like and as a dental material for orthodontic appliances such as orthodontic brackets. Further, the zirconia sintered body of the present embodiment can be applied to known use of zirconia sintered bodies, such as a structural material, a decoration material, and an optical material.

Examples of other embodiments of the zirconia sintered body of the present disclosure include the following.

A zirconia sintered body comprising yttria and zirconia, containing yttria in a content ranging from 4.5 mol % or more to 6.5 mol % or less and zirconia as the remainder, and including crystal grains of different yttria concentrations.

A zirconia sintered body comprising yttria and zirconia, containing yttria in a content ranging from 4.5 mol % or more to 6.5 mol % or less and zirconia as the remainder, in which a number ratio of crystal grains with the yttria concentration ranging from 3.0 mol % or higher to 4.0 mol % or less to all the crystal grains is 10% or higher and 50% or less.

A zirconia sintered body comprising yttria and zirconia, containing yttria in a content ranging from 4.5 mol % or more to 6.5 mol % or less and zirconia as the remainder, in which the difference in the concentration among the crystal grains is 3 mol % or higher and 7 mol % or less.

A zirconia sintered body consisting of yttria and zirconia, containing yttria in a content ranging from 4.5 mol % or more to 6.5 mol % or less and zirconia as the remainder, and including crystal grains of different yttria concentrations.

A zirconia sintered body comprising yttria and zirconia, containing yttria in a content ranging from 4.5 mol % or more to 6.5 mol % or less and zirconia as the remainder, and satisfying at least one of conditions such that the sintered body includes crystal grains of different yttria concentrations, that a number ratio of crystal grains with the yttria concentration ranging from 3.0 mol % or higher to 4.0 mol % or less to all the crystal grains is 10% or higher and 50% or less, and that the difference in the concentration among the crystal grains is 3 mol % or higher and 7 mol % or less.

Next, a production method of the zirconia sintered body of the present embodiment will be described.

Examples of preferable production method of the zirconia sintered body of the present embodiment include a production method of a zirconia sintered body including a process of sintering a green body including a zirconia powder which includes a yttria source and zirconia, in which the content of the yttria source is 4.5 mol % or more and 6.5 mol % or less and the remainder is zirconia, a total ratio of tetragonal s and cubic crystals to the entire crystal phase of zirconia is 90% or less, a BET specific surface area is 7.5 m$^2$/g or more and 15 m$^2$/g or less, and an average crystallite size is 325 Å or greater.

The green body used in the production method of the present embodiment includes a yttria source and zirconia, in which the content of the yttria source is 4.5 mol % or more and 6.5 mol % or less and the remainder is zirconia, a total ratio of tetragonal and cubic crystals to the entire crystal phase of zirconia is 90% or less, and a BET specific surface area is 7.5 m$^2$/g or more and 15 m$^2$/g or less. By using the green body including the zirconia powder described above for the sintering, a closely packed green body can be obtained even if the sintering is sintering implemented by a sintering method in which the rate of temperature increase in the sintering is high (e.g., at 250° C./h or higher) or atmospheric sintering.

The zirconia powder comprises an yttria source and zirconia. The yttria source is either yttria or a precursor thereto, and is preferably yttria. Examples of the precursor to yttria include at least one of yttrium chloride and yttrium nitrate, and yttrium chloride is preferable. It is preferable if the yttria source be dissolved in zirconia as a solid solution. The entire yttria source may be dissolved in zirconia as a solid solution. It is preferable if the zirconia powder include no yttria source not dissolved in zirconia as a solid solution.

The content of the yttria source may be equivalent to the content of yttria in the zirconia sintered body to be produced. The range of the content of the yttria source in the zirconia powder may be 4.5 mol % or higher and 6.5 mol % or less, higher than 4.5 mol % and 6.0 mol % or less, 4.7 mol % or higher and 5.8 mol % or less, or 4.8 mol % or higher and 5.5 mol % or less, for example. In another embodiment, the content of the yttria source may be 5.0 mol % or higher and 6.0 mol % or less, or 5.0 mol % or higher and 5.8 mol % or less, for example.

The content of the yttria source in the zirconia powder is a ratio (mol %) of yttrium (Y) equivalent to $Y_2O_3$ to a total value for the content of zirconium (Zr) equivalent to $ZrO_2$ and the content of yttrium (Y) equivalent to $Y_2O_3$ in the zirconia powder, which can be calculated by using the following expression: $\{Y_2O_3 \text{ [mol]}/(ZrO_2+Y_2O_3) \text{ [mol]}\} \times 100$.

The zirconia powder may contain an alumina source. The alumina source may be at least one of alumina and a precursor thereto. For the alumina source, alumina is preferable, and α-alumina is more preferable. The content of the alumina source in the zirconia powder may be equivalent to the content of alumina in the zirconia sintered body to be produced. The content of the alumina source in the zirconia powder may be 0% by mass or higher and 0.2% by mass or less, 0% by mass or higher and 0.15% by mass or less, 0% by mass or higher and 0.1% by mass or less, higher than 0% by mass and 0.2% by mass or less, 0.005% by mass or higher and 0.15% by mass or less, 0.01% by mass or higher and 0.12% by mass or less, or 0.015% by mass or higher and 0.1% by mass or less, for example.

The content of the alumina source in the zirconia powder is a mass ratio (% by mass) of aluminum (Al) equivalent to $Al_2O_3$ to a total value for the content of zirconium (Zr) equivalent to $ZrO_2$ and the content of yttrium (Y) equivalent to $Y_2O_3$ in the zirconia powder, which can be calculated by using the following expression: $\{Al_2O_3 \, [g]/(ZrO_2+Y_2O_3+Al_2O_3) \, [g]\} \times 100$.

The zirconia powder may include a colorant to color the zirconia sintered body to be produced in a desired color. The colorant is an element having a function for coloring zirconia, and may be an element having a function for suppressing phase transition of zirconia. Specific examples of the colorant include at least one of transition metal elements and lanthanoid rare earth elements; preferable examples of the colorant include one or more selected from the group consisting of iron, cobalt, nickel, manganese, praseodymium, neodymium, europium, gadolinium, terbium, erbium, and ytterbium; more preferable examples of the colorant include one or more selected from the group consisting of iron, cobalt, manganese, praseodymium, neodymium, terbium, and erbium; and yet more preferable examples include one or more selected from the group consisting of iron, cobalt and erbium.

The zirconia powder may include inevitable impurities such as hafnia ($HfO_2$). The content of hafnia as the inevitable impurity may be 2.0% by mass or less, for example. However, it is preferable if the zirconia powder satisfy at least one of the following conditions: the content of magnesium expressed in terms of magnesia (MgO) is 0 ppm by mass or higher and 500 ppm by mass or less; the content of silicon expressed in terms of silica ($SiO_2$) is 0 ppm by mass or higher and 500 ppm by mass or less; and the content of titanium expressed in terms of titania ($TiO_2$) is 0 ppm by mass or higher and 500 ppm by mass or less, and it is preferable if the content of magnesium, silicon, and titan be 0 ppm by mass or higher and 500 ppm by mass or less.

For the zirconia powder, a total ratio of tetragonal and cubic crystals to the crystal phase (hereinafter also referred to as "T+C phase ratio") may be 90% or less, preferably 85% or less, 80% or less, or 75% or less. With the configuration satisfying the T+C phase ratio in the above range and an average crystallite size described below, the production method of the present embodiment is capable of increasing the mechanical strength of the zirconia sintered body obtained after the sintering. The T+C phase ratio may be 50% or higher, preferably 55% or higher or 60% or higher. In the present embodiment, phases of the crystal phase of the zirconia powder other than the phase with the T+C phase ratio may be considered as monoclinic crystal. The ratio of the monoclinic crystal in the crystal phase (hereinafter also referred to as "M-phase ratio") may be a ratio higher than 10%, a ratio higher than 15%, a ratio higher than 20%, or a ratio higher than 25%; or a ratio less than 50%, a ratio less than 45%, or a ratio less than 40%, for example. Note that the T+C phase ratio tends to easily rise if the yttria content rises.

The T+C phase ratio for the zirconia powder can be calculated by a method similar to the method used in calculating the tetragonal+cubic crystal ratio ($f_{T+C}$), and the M-phase ratio can be calculated by a method similar to the method used in calculating the monoclinic crystal ratio ($f_M$). In addition, XRD patterns of the zirconia powder can be obtained by measurement performed under conditions similar to those for the XRD measurement for the zirconia sintered body.

The BET specific surface area of the zirconia powder is 7.5 m²/g or more and 15 m²/g or less. If the content of the yttria source is as described above and if the BET specific surface area is lower than the above range, the sintering rate may become too low, while if the BET specific surface area is higher than the above range, the sintering rate may become too high. In both of the above cases, it becomes more difficult to obtain a fully densified sintered body by normal-pressure sintering, especially by atmospheric sintering. The close packing of the sintered body tends to be more promoted even if sintering at a high rate of temperature increase is applied, and thus it is preferable if the BET specific surface area be 8 m²/g or higher and 15 m²/g or less, 9 m²/g or higher and 13 m²/g or less, or 9.5 m²/g or higher and 11 m²/g or less. In another embodiment, the BET specific surface area may be 9.5 m²/g or higher or 10 m²/g or higher, or 12 m²/g or less or 11 m²/g or less or 10.5 m²/g or less.

In the present embodiment, the BET specific surface area is a BET specific surface area measured by a method in compliance with JIS Z 8830, and may be measured by a BET single-point method by a carrier gas method which uses nitrogen as the adsorption gas. Specific examples of the conditions for measuring the BET specific surface area include the following conditions.

Adsorption medium: $N_2$
Adsorption temperature −196° C.
Preprocessing conditions Processing for 30 minutes at 250° C. in the atmosphere The BET specific surface area can be measured by using a common apparatus (e.g., Flowsorb III 2305, a product of Shimadzu Corporation).

The average crystallite size of the zirconia powder may be 325 Å or greater, preferably be 330 Å or greater, 335 Å or greater, or 340 Å or greater. With the configuration using the zirconia powder that satisfies the condition for the average crystallite size in the above range as well as the above condition for the T+C phase ratio, the present embodiment enables growth of the crystal grains and elimination of the pores to efficiently advance during the sintering, and thus the present embodiment is capable of obtaining a zirconia sintered body with a high translucency and a high mechanical strength even if the sintering is implemented by normal-pressure sintering and further by atmospheric sintering. Due to similar reasons, it is preferable if the average crystallite size be 450 Å or less, 400 Å or less, 398 Å or less, or 380 Å or less. Note that it becomes easier for the average crystallite size to increase as the content of yttria becomes higher.

In the present embodiment, the average crystallite size is a crystallite size calculated based on the XRD peak in the XRD pattern of the zirconia powder in which the tetragonal face (111) and the cubic crystal face (111) are overlapped (hereinafter also referred to as "main XRD peak"), which is a value calculated by using the following expression.

$$D = \kappa \lambda / \beta \cos \theta$$

In the above expression, D is an average crystallite size (Å), κ is a Scherrer constant (κ=1), λ is the wavelength of the measured X-ray (If the CuKα ray is the radiation source, then λ=0.15418 nm), β is a half-width (°) for the main XRD peak, and θ is a Bragg angle for the main XRD peak. Note that β is a value for the half-width of the main XRD peak obtained by performing profile fitting on the XRD pattern processed by smoothing and background elimination using divided pseudo-Voigt function. The profile fitting can be implemented by using an analysis program attached to the X-ray diffraction apparatus (e.g., Integrated X-ray powder diffraction software PDXL Ver. 2.2, a product of Rigaku Corporation) and the like.

It is preferable if the mean particle size be 0.35 μm or greater and 0.5 μm or less more preferably 0.4 μm or greater and 0.45 μm or less.

In the present embodiment, the mean particle size is D50 in the distribution of the volume particle size of the powder measured by a wet method, which can be measured with a common apparatus (e.g., MT3300 EX II, a product of MicrotracBEL Corporation). For the measurement sample, a slurry prepared by dispersing a powder from which sluggish flocculation has been eliminated by dispersion processing such as sonication in pure water may be used. It is preferable if the measurement of the distribution of the volume particle size by the wet method be performed using a slurry controlled to be acidic (e.g., at the pH of 3.0 to 6.0).

A desired method may be used for the production method of the zirconia powder, and the zirconia powder production method may be a production method including a process of crushing a composition containing zirconia sol and a yttria source treated by heat treatment at a temperature ranging from 950° C. or higher to 1,250° C. or lower, for example. It is preferable if the zirconia sol be a zirconia sol obtained by either a hydrothermal synthesis method or a hydrolysis method, more preferably a zirconia sol obtained by a hydrolysis method. The BET specific surface area tends to be smaller as the above heat treatment temperature becomes higher.

To improve the operability of the zirconia powder, the zirconia powder may be a granulated powder (hereinafter also referred to as "powder granule"). The granule size of the powder granule may be 30 μm or greater and 80 μm or less for example. The granulation may be implemented by a method in which the zirconia powder is loosely flocculated, and granulation methods such as spray granulation may be used, for example.

In the present embodiment, the granulation size is D50 in the distribution of the volume grain sizes measured by a dry method, and the measurement can be implemented by using a common apparatus (e.g., MT3100 II, a product of MicrotracBEL Corporation). For the measurement sample, a powder in the sluggish flocculation state not treated by dispersion treatment such as sonication may be used as it is.

It is preferable if the zirconia powder include zirconia powders of different yttria contents, and it is more preferable if the zirconia powder include zirconia powder particles containing yttria by a specific content and another zirconia powder particles containing yttria by a content different from the specific content of yttria in the above zirconia powder particles (the zirconia powder particles included in the zirconia powder containing yttria by higher yttria content will be hereinafter also referred to as "high-Y particles", and the zirconia powder particles included in the zirconia powder containing yttria by lower yttria content will be hereinafter also referred to as "low-Y particles"). With this configuration, the translucency of the zirconia sintered body to be obtained tends to increase even if the sintering is implemented by sintering at a relatively low sintering temperature.

In the present embodiment, for the zirconia powder which "includes zirconia powder particles of different yttria contents", the yttria content of the zirconia powder particles included in the zirconia powder may be different for some of the zirconia powder particles, and it is not necessary that the yttria content is different for all the zirconia powder particles included in the zirconia powder particles.

In another embodiment, it is preferable if the zirconia powder include two or more zirconia powder particles and if the content of yttria included in a first zirconia powder particle be different from the content of yttria included in a second zirconia powder particle. In yet another embodiment, it is preferable if the zirconia powder be a mixed powder of a zirconia powder containing yttria by a specific content and another zirconia powder containing yttria by a content different from the yttria content of the above zirconia powder.

The yttria content for the low-Y particle may be 1.0 mol % or higher, 1.3 mol % or higher, 1.5 mol % or higher, 1.8 mol % or higher, 2.0 mol % or higher, or 2.3 mol % or higher, and 5.0 mol % or less, 4.5 mol % or less, 4.2 mol % or less, 3.5 mol % or less, or 3.2 mol % or less, for example. The yttria content for the high-Y particle may be higher than 5.0 mol %, 5.2 mol % or higher, 5.5 mol % or higher, or 6.0 mol % or higher, and 10.0 mol % or less, 9.0 mol % or less, 8.5 mol % or less, 8.0 mol % or less, or 7.0 mol % or less, for example.

It is preferable if the difference between the yttria content for the high-Y particle and the yttria content for the low-Y particle (hereinafter also referred to as "yttria content difference") be larger than 3.0 mol %. With this configuration, it becomes easier for the zirconia powder to satisfy the T+C phase ratio and the average crystallite size described above. It is preferable if the yttria content difference be 3.3 mol % or larger, 3.5 mol % or larger, 4.0 mol % or larger, or 4.3 mol % or larger. The yttria content difference may be 7.5 mol % or less, 7.0 mol % or less, or 6.5 mol % or less, for example. It is preferable if the yttria content difference be 3.8 mol % or larger and 6.5 mol % or less because the translucency and the mechanical strength of the zirconia sintered body obtained by sintering in an air atmosphere tend to increase if the yttria content difference is in this range.

In the present embodiment, the yttria content difference can be measured by scanning transmission electron microscopy-energy dispersive X-ray spectrometry (STEM-EDS) measurement on the zirconia powder. In another embodiment, if a known production method is used for the production of the zirconia powder, the yttria content difference can be calculated from the difference of the content of yttria included in precursor powders used for the production.

In the STEM-EDS measurement on the zirconia powder, the powder particles observed in a transmission electron microscopy (TEM) observation view with no overlap of the zirconia powder particles are irradiated with electron rays to obtain EDS spectra of each zirconia powder particle. Based on each of the obtained EDS spectra, the content of yttria ($=Y_2O_3/(ZrO_2+Y_2O_3$: mol %) included in each powder particle may be determined from the peak intensity of yttrium in relation to the total of the peak intensity of yttrium and the peak intensity of zirconium.

For the difference between the concentration of yttria, the difference between the largest value and the smallest value for the concentration of yttria included in a sufficient number of zirconia powder particles (10 or more particles, for example, and preferably 30±5 particles) determined by the STEM-EDS measurement may be used.

In the present embodiment, the STEM-EDS measurement can be implemented by a commercial apparatus (e.g., TEM: JEM-2100F, a product of JEOL Ltd., EDS: JED-2300T, a product of JEOL Ltd.).

The T+C phase ratio for the low-Y particle is preferably 0% or higher or 1% or higher, and 50% or less, 40% or less, 20% or less, or 10% or less, for example. The T+C phase ratio for the high-Y particle is preferably greater than 50%, 70% or higher, or 90% or higher, and 100% or less, for example.

A desired method may be used for the production method of the zirconia powder containing zirconia powder particles containing yttria by different contents, and it is preferable if a mixture of two or more zirconia powders containing yttria by different yttria contents (hereinafter also referred to as "precursor powder", respectively) be used to obtain the physical properties of the zirconia powder to be used in the production method of the present embodiment. With this configuration, a zirconia powder including a mixed powder is obtained. For the method of the mixing, any method may be used by which the precursor powders can be sufficiently mixed. Examples of the mixing method include at least one of dry mixing and wet mixing. A wet mixing method may be preferably used, and more preferably, the precursor powders may be mixed in a water solvent.

The rate of mixture of the precursor powders may be appropriately adjusted by adjusting the content of yttria included in the precursor powders and the zirconia powder to be prepared, and may range from 1% by mass:99% by mass to 99% by mass:1% by mass; 20% by mass:80% by mass to 80% by mass:20% by mass; or 35% by mass:65% by mass to 65% by mass:35% by mass, for example. The zirconia powder may include a mixed powder containing two precursor powders, and may alternatively include a mixed powder containing three or more precursor powders.

To obtain a zirconia powder with homogeneous physical properties, it is preferable if the precursor powders respectively have the BET specific surface area and the mean particle size similar t those of the zirconia powder to be prepared, and the precursor powders may respectively have the BET specific surface area and the mean particle size values of the above zirconia powder. The BET specific surface area for the high-yttria powder may preferably be larger than that for the low-yttria powder (e.g., the BET specific surface area for the high-yttria powder may be 0.5 $m^2/g$ or larger and 2.0 $m^2/g$ or smaller).

The green body may contain a binder. If a binder is included, the shape retaining property of the green body can be increased. For the binder included in the green body, a known binder used for molding of ceramics can be used, and an organic binder is preferable. Examples of such an organic binder include at least one selected from the group consisting of polyvinyl alcohol, polyvinyl butyrate, wax, and acrylic resin, preferably include at least one selected from the group consisting of polyvinyl alcohol and acrylic resin, and more preferably include acrylic resin. In the present embodiment, the acrylic resin is a polymer including at least one of acrylate and methacrylate. Specific examples of the acrylic resin include one or more selected from the group consisting of polyacrylic acid, polymethacrylic acid, acrylic acid copolymer, and methacrylic acid copolymer, and derivatives thereof.

The green body used in the production method of the present embodiment may be shaped in a desired shape. Examples of the shape of the green body include at least one selected from the group consisting of a cube-like shape, rectangular shape, polyhedral shape, columnar shape, cylindrical shape, disk-like shape, and substantially spherical shape, and a shape similar to the shape of the zirconia sintered body to be produced, such as a shape of a dental prosthetic material, considering thermal contraction that may occur during the sintering.

The green body may have a relative density in a range of 45% or higher and 55% or less, preferably in a range of 48% or higher and 52% or less, for example.

The relative density of the green body is a ratio of a measured density to the theoretical density. The relative density of the green body can be determined by using a density (g/cm$^3$), which is obtained from a mass determined by measurement of a mass in relation to the volume obtained from the dimension determined by measuring the dimension, as the measured density and by using a method similar to the method for determining the relative density of the zirconia sintered body.

A desired method may be used for the production method of the green body used in the production method of the present embodiment, and a known method of molding ceramics can be applied. Examples of the green body molding method include at least one selected from the group consisting of uniaxial press molding, cold isostatic press molding, slip casting, and injection molding. For easy implementation of the molding, at least one of uniaxial press molding and cold isostatic press molding is preferably used as the molding method, and it is more preferable if the molding be implemented by cold isostatic press molding performed after uniaxial press molding. With this configuration, the present embodiment is capable of obtaining a green body which retains a shape formed by physical coagulation of the green body, i.e., the zirconia powder. The pressure for the uniaxial press molding may be 15 MPa or higher and 150 MPa or less and the pressure for the cold isostatic press molding may be 90 MPa or higher and 400 MPa or less, for example. The density of the green body to be obtained may more easily become higher as the pressure for the molding becomes higher. The green body obtained by the above production method may be regarded as a green body including the zirconia powder.

In an embodiment in which the green body includes a binder, the present embodiment may include a process of eliminating the binder, i.e., a debinding process, which is performed prior to the sintering. A desired method may be used to implement the binder elimination method, and examples of the binder elimination method include heat treatment performed at a temperature in a range from 400° C. to a temperature lower than 900° C. in the atmosphere.

In the above process of sintering the component (hereinafter also referred to as "sintering process"), the green body may be a green body having a structure at the early stage of the sintering, i.e., a pre-sintered body. Examples of the structure at the early stage of the sintering include a structure in which necking is formed by the zirconia particles, and the pre-sintered body may include fused zirconia particles. The pre-sintered body may be shaped in a desired shape formed by working by using computer-aided designing (CAD), computer-aided manufacturing (CAM), or the like, and thus a zirconia sintered body having a desired shape can be more easily obtained.

Examples of the conditions for the pre-sintering include heat treatment at a temperature lower than the sintering temperature for zirconia, i.e., heat treatment performed in an air atmosphere at a temperature ranging from 900° C. or higher to lower than 1,200° C. for 0.5 hours or longer and 10 hours or less; preferably include heat treatment performed in an air atmosphere at a temperature ranging from 1,000° C. or higher to 1,150° C. or lower for 1 hour or longer and 10 hours or less.

The pre-sintered body is obtained by heat treatment on a green body obtained by molding the zirconia powder. Because the properties such as the BET specific surface area, the T+C phase ratio, and the crystallite size may change during the heat treatment, the physical properties of the compact (green body) may not be identical to those of the pre-sintered body in most cases. Examples of such a pre-sintered body include a pre-sintered body comprising a yttria source and zirconia and containing the yttria source by a content of 4.5 mol % or higher and 6.5 mol % or less and zirconia as the remainder; and a pre-sintered body containing the yttria source by a content of 4.5 mol % or higher and 6.5 mol % or less, containing zirconia as the remainder, and including fused particles.

In the pre-sintered body obtained by the production method of the present embodiment, the largest value for the frequency in the distribution of the yttria concentration obtained by element quantitative analysis of the energy dispersion spectra (hereinafter also referred to as "maximum frequency") may be less than 30%, 28% or less, or 15% or less, for example. The maximum frequency may be 8% or higher or 10% or higher, for example.

For the pre-sintered body, the difference between the largest value and the smallest value for the yttria concentration obtained by the element quantitative analysis of the energy dispersion spectra may be larger than 3.0 mol %, 3.3 mol % or larger, 3.5 mol % or larger, 4.0 mol % or larger, or 4.3 mol % or larger, and 7.5 mol % or smaller, 7.0 mol % or smaller or 6.5 mol % or smaller, for example.

The element quantitative analysis of the energy dispersion spectra (hereinafter also referred to as "EDS spectra") may be implemented by a method in which EDS spectra are obtained from a scanning electron microscopy (hereinafter also referred to as "SEM") observation view for the pre-sintered body and then the intensity levels of the characteristic X-rays for zirconium (Zr) and yttrium (Y) in the obtained EDS spectra are determined. The quantitative analysis of the EDS spectra may be implemented by measurement at 40,000 points (preferably at 50,000±10,000 points) or more. For the yttrium concentration, a rate of the intensity of yttrium to the intensity of zirconium (hereinafter also referred to as "Y/Zr ratio") may be used. The yttrium concentration distribution is a distribution of concentration of yttrium illustrated using a given yttrium concentration sectioned into concentration subranges, and may be a yttrium concentration distribution illustrating the Y/Zr ratio using concentration subranges respectively provided per 0.5 atm %. The frequency is a rate (%) of the measurement points corresponding to each yttrium concentration in relation to the total number of measurement points in the quantitative analysis of EDS spectra.

For the method of the sintering in the sintering process, a known sintering method can be applied, such as at least one selected from the group consisting of normal-pressure sintering, pressure sintering, and vacuum sintering. However, normal-pressure sintering is preferable as the sintering method because it is widely applied to the production of dental prosthetic materials, and a method using normal-pressure sintering only, i.e., a sintering method that does not use pressure sintering or vacuum sintering, is more preferable. The zirconia sintered body according to the present embodiment can be obtained from the green body used in the production method of the present embodiment as a sintered body known as normal-pressure sintered body even if the sintering method is sintering which uses normal-pressure sintering only. In the present embodiment, the term "normal-pressure sintering" is a method of sintering an object of the sintering (such as green body and pre-sintered body) is heated without applying any external force during the sintering.

Examples of the conditions for the sintering include the following. The sintering temperature may be 1,200° C. or higher and 1,600° C. or lower, and may preferably be 1,300° C. or higher and 1,580° C. or lower, 1,400° C. or higher and 1,560° C. or lower, or 1,430° C. or higher and 1,560° C. or lower. In another embodiment, the sintering temperature may be 1,450° C. or higher and 1,650° C. or lower, and may preferably be 1,500° C. or higher and 1,650° C. or lower, or 1,550° C. or higher and 1,650° C. or lower. The rate of temperature rise up to the sintering temperature may be 50° C./h or higher and 800° C./h or lower, for example, and may preferably be 100° C./h or higher and 800° C./h or lower, 150° C./h or higher and 800° C./h or lower, or 150° C./h or higher and 700° C./h or lower. The retention time for retaining the sintering temperature (hereinafter also referred to as "sintering time") may differ for different sintering temperatures, and may be 1 hour or longer and 5 hours or less, 1 hour or longer and 3 hours or less, or 1 hour or longer and 2 hours or less. For the sintering atmosphere, atmospheres other than reducing atmosphere are preferable, and at least either of an oxygen atmosphere and an air atmosphere is more preferable. If sintering in an oxygen atmosphere is used, elimination of the pores may easily advance, and thus the parallel light transmittance of the zirconia sintered body to be obtained may become too high. Accordingly, an air atmosphere if yet more preferable for the sintering atmosphere. The air atmosphere is an atmosphere primarily including nitrogen and oxygen, and examples of the air atmosphere include an atmosphere in which the oxygen concentration is 18 to 23 vol. %.

EXAMPLES

Now, the present embodiment will be described below with reference to Examples. However, the present embodiment is not limited to the Examples.

(XRD Measurement)

XRD patterns of the powder sample and the sintered body sample were obtained by XRD measurement under the following conditions.

Radiation source: CuKα ray ($\lambda_{=0.15418}$ nm):
Measurement mode: Continuous scanning
Scan speed: 4°/min
Step width: 0.02°
Measurement range: 2θ=26° to 33°

For the XRD measurement, a common X-ray diffraction apparatus (apparatus name: MiniFlex, a product of Rigaku Corporation) was used. An analysis program attached to the apparatus (software name: Integrated X-ray powder diffraction software PDXL Ver. 2.2, a product of Rigaku Corporation) was used. The obtained patterns were processed by smoothing and background elimination, and then the XRD patterns were analyzed by profile fitting using divided pseudo-Voigt function. Note that β values were calculated without correcting the mechanical spread width because the average crystallite size of the zirconia powder is small and thus the impact from the mechanical spread width of the XRD apparatus for calculation of the average crystallite size is minute.

(Composition Analysis)

The composition of the sample was measured by inductively coupled plasma (ICP) spectrometry.

(BET Specific Surface Area)

Nitrogen was used as the adsorption gas to measure the BET specific surface area of the powder sample, using a fluid specific surface area automatic measuring apparatus (apparatus name: Flowsorb III 2305, a product of Shimadzu Corporation) was used to measure the BET specific surface area of the powder sample. Prior to the measurement of the BET specific surface area, the powder sample was deaerated at 250° C. for 30 minutes in the atmosphere.

(Mean Particle Size)

The mean particle size of the powder sample was measured using a Microtrac particle size analyzer (apparatus name: MT3300 EX II, a product of MicrotracBEL Corporation).

As the preprocessing, the sample powder was suspended in distilled water to obtain a slurry, and the resultant was dispersed for 3 minutes using a sonication homogenizer (apparatus name: US-150T, a product of Nissei Corporation).

(Average Crystal Grain Size)

The average crystal grain size of the zirconia sintered body was calculated by a planimetric method which uses SEM observation views. As the measurement sample, a sample obtained by treating a zirconia sintered body having a surface roughness of Ra≤0.02 μm treated in the atmosphere at a temperature lower than the sintering temperature by 50° C. was used, and the sample was observed by SEM observation at a magnification power at which about 200 crystal grains can be observed (i.e., at powers ranging from 5,000 to 10,000).

A circle with a known area was drawn on the obtained SEM observation view, the number of crystal grains in the circle (Nc) and the number of crystal grains on the circumstance of the circle (Ni) were measured, the total number of the crystal grains (Nc+Ni) was adjusted to be 250±50, and the average crystal grain size was calculated by using the following expression.

$$\text{Average crystal grain size} = 2/[\pi \times \{(Nc+(\tfrac{1}{2}) \times Ni)/(A/M^2)\}]^{0.5}$$

(Relative Density)

The relative density of the sample of the sintered body was calculated as a rate (%) of a measured density to the theoretical density. The measured density was calculated from the ratio (g/cm$^3$) of the volume measured by Archimedes method to the mass measured by mass measurement using a digital balance. The theoretical density was calculated by using the above expressions (1) to (4).

(Light Transmittance and Parallel Light Transmittance)

The light transmittance (total light transmittance) and the parallel light transmittance were measured by using a hazemeter (apparatus name: NDH4000, a product of Nippon Denshoku Industries Co., Ltd.) and a D65 light source, using a method compliant with a method compliant with JIS K 7361-1.

For the measurement sample, a 1-mm thick disk-like sintered body ground on both surfaces to achieve the surface roughness Ra≤0.02 μm was used.

(PT/TT Ratio)

The PT/TT ratio was measured by using a method which uses a 1-mm thick disk-like zirconia sintered body with the surface roughness Ra≤0.02 μm on both surfaces as the measurement sample and a common UV-VIS spectrophotometer (e.g., Spectrophotometer V-650, a product of JASCO Corporation) as the measurement apparatus. The measurement conditions were as follows.

Measurement method: UV-VIS spectrophotometry
   Measurement system: Double-beam system
   Light source: Halogen lamp
   Range of measurement wavelength: 400 nm-700 nm
   Wavelength step: 0.5 nm (Three-Point Bending Strength)

The three-point bending strength was measured by using a method compliant with JIS R 1601. The measurement was performed 10 times to obtain an average value. The measurement was performed on a sample of a 4 mm-wide, 3 mm-thick column-like sintered body at the distance between support points of 30 mm. The crosshead speed was set at 0.5 mm/min.

Example 1

A hydrated zirconia sol obtained by hydrolysis reaction of an aqueous solution of zirconium oxychloride and yttria were mixed, and the obtained mixture was dried and then treated by heat treatment at 1,160° C. for 2 hours to obtain a yttria-containing zirconia powder containing yttria by a content of 2.5 mol %. The yttria-containing zirconia powder obtained in the above-described manner, α-alumina with the mean particle size of 0.3 μm, and pure water was mixed to obtain a slurry including a zirconia powder (precursor powder 1) including alumina by a content of 0.05% by mass and yttria by a content of 2.5 mol % was prepared. In the obtained zirconia powder (precursor powder 1), the T+C phase ratio was 18%, the average crystallite size was 196 Å, and the BET specific surface area was 10.0 m$^2$/g.

Moreover, by using a method similar to the above method except that the yttria content was 8.5 mol %, a slurry was prepared including a zirconia powder (precursor powder 2) including alumina by a content of 0.05% by mass and yttria by a content of 8.5 mol %. In the obtained zirconia powder (precursor powder 2), the T+C phase ratio was 100%, the average crystallite size was 397 Å, and the BET specific surface area was 11.3 m$^2$/g.

The difference in the yttria content between the yttria content for the slurry of the precursor powder 1 and that for the slurry of the precursor powder 2 was 6.0 mol %. The slurries were mixed to adjust the yttria content to 5.2 mol %, and then the obtained mixture was dried to obtain a zirconia powder including alumina by a content of 0.05% by mass and yttria by a content of 5.2 mol %.

The zirconia powder was molded by uniaxial pressure press molding at a pressure of 19.6 MPa and treated by CIP treatment at a pressure of 196 MPa to obtain a green body. The obtained green body was pre-sintered at 1,000° C. in an air atmosphere for 1 hour to obtain a pre-sintered body. In the obtained pre-sintered body, the maximum frequency was 12%, and the difference between the highest value and the lowest value for the yttria concentration was 5.5 mol %. Then the obtained pre-sintered body was sintered at the rate of temperature increase of 600° C./h and at the sintering temperature of 1,450° C. for 2 hours in an air atmosphere to obtain a zirconia sintered body according to the present Example.

Example 2

By using a method similar to the method of preparing the precursor powder 1 of Example 1 except that yttria was mixed to adjust the yttria content to 2.0 mol %, a slurry was prepared including a zirconia powder (precursor powder 1) including alumina by a content of 0.05% by mass and yttria by a content of 2.0 mol %. In the obtained zirconia powder (precursor powder 1), the T+C phase ratio was 4%, the average crystallite size was 169 Å, and the BET specific surface area was 8.6 m$^2$/g.

By using a method similar to the method of preparing the precursor powder 2 of Example 1 except that yttria was mixed to adjust the yttria content to 6.5 mol %, a slurry was prepared including a zirconia powder (precursor powder 2) including alumina by a content of 0.05% by mass and yttria by a content of 6.5 mol %. In the obtained zirconia powder (precursor powder 2), the T+C phase ratio was 100%, the average crystallite size was 350 Å, and the BET specific surface area was 10.3 m$^2$/g.

The difference in the yttria content between the yttria content for the slurry of the precursor powder 1 and that for the slurry of the precursor powder 2 was 4.5 mol %. The slurries were mixed to adjust the yttria content to 5.2 mol %, and then the obtained mixture was dried to obtain a zirconia powder including alumina by a content of 0.05% by mass and yttria by a content of 5.2 mol %.

The obtained zirconia powder was molded, pre-sintered, and sintered by a method similar to the method of Example 1 except that the zirconia powder obtained by the method according to the present Example was used to obtain a zirconia sintered body of the present Example.

Example 3

By using a method similar to the method of Example 1 except that yttria was mixed to adjust the yttria content to 1.5 mol %, a slurry was prepared including a zirconia powder (precursor powder 1) including alumina by a content of 0.05% by mass and yttria by a content of 1.5 mol %. In the obtained zirconia powder (precursor powder 1), the T+C phase ratio was 0% and the BET specific surface area was 7.9 m$^2$/g.

By using a method similar to the method of preparing the precursor powder 2 of Example 1, a slurry was prepared including a zirconia powder (precursor powder 2) including alumina by a content of 0.05% by mass and yttria by a content of 8.5 mol %.

The difference in the yttria content between the yttria content for the slurry of the precursor powder 1 and that for the slurry of the precursor powder 2 was 7.0 mol %. The slurries were mixed to adjust the yttria content to 5.2 mol %, and then the obtained mixture was dried to obtain a zirconia powder including alumina by a content of 0.05% by mass and yttria by a content of 5.2 mol %.

The obtained zirconia powder was molded, pre-sintered, and sintered by a method similar to the method of Example 1 except that the zirconia powder obtained by the method according to the present Example was used to obtain a zirconia sintered body of the present Example.

Example 4

By using a method similar to the method of preparing the precursor powder 1 of Example 1 except that yttria was mixed to adjust the yttria content to 1.5 mol % and that the zirconia powder was treated by heat treatment at 1,130° C. for 2 hours in the atmosphere, a slurry was prepared including a zirconia powder (precursor powder 1) including alumina by a content of 0.05% by mass and yttria by a content of 1.5 mol %. In the obtained zirconia powder, the T+C phase ratio was 0% and the BET specific surface area was 11.4 m$^2$/g.

By using a method similar to the method of preparing the precursor powder 2 of Example 1 except that yttria was mixed to adjust the yttria content to 5.5 mol %, a slurry was prepared including a zirconia powder (precursor powder 2) including alumina by a content of 0.05% by mass and yttria by a content of 5.5 mol %. In the obtained zirconia powder, the T+C phase ratio was 97%, the average crystallite size was 340 Å, and the BET specific surface area was 10.0 m$^2$/g.

The difference in the yttria content between the yttria content for the slurry of the precursor powder 1 and that for the slurry of the precursor powder 2 was 4.0 mol %. The slurries were mixed to adjust the yttria content to 5.2 mol %, and then the obtained mixture was dried to obtain a zirconia powder including alumina by a content of 0.05% by mass and yttria by a content of 5.2 mol %.

The obtained zirconia powder was molded, pre-sintered, and sintered by a method similar to the method of Example 1 except that the zirconia powder obtained by the method according to the present Example was used to obtain a zirconia sintered body of the present Example. In the obtained pre-sintered body, the maximum frequency was 26% and the difference between the highest value and the lowest value for the yttrium concentration was 3.3 mol %.

Example 5

By using a method similar to the method of Example 1 except that yttria was mixed to adjust the yttria content to 3.0 mol %, a slurry was prepared including a zirconia powder (precursor powder 1) including alumina by a content of 0.05% by mass and yttria by a content of 3.0 mol %. In the obtained zirconia powder, the T+C phase ratio was 42%, the average crystallite size was 236 Å, and the BET specific surface area was 9.5 m$^2$/g.

By using a method similar to the method of preparing the precursor powder 2 of Example 1 except that yttria was mixed to adjust the yttria content to 6.5 mol %, a slurry was prepared including a zirconia powder (precursor powder 2) including alumina by a content of 0.05% by mass and yttria by a content of 6.5 mol %. In the obtained zirconia powder, the T+C phase ratio was 100%, the average crystallite size was 350 Å, and the BET specific surface area was 10.3 m$^2$/g.

The difference in the yttria content between the yttria content for the slurry of the precursor powder 1 and that for the slurry of the precursor powder 2 was 3.5 mol %. The slurries were mixed to adjust the yttria content to 5.2 mol %, and then the obtained mixture was dried to obtain a zirconia powder including alumina by a content of 0.05% by mass and yttria by a content of 5.2 mol %.

The obtained zirconia powder was molded, pre-sintered, and sintered by a method similar to the method of Example 1 except that the zirconia powder obtained by the method according to the present Example was used to obtain a zirconia sintered body of the present Example.

Example 6

By using a method similar to the method of Example 1 except that yttria was mixed to adjust the yttria content to 2.5 mol %, a slurry was prepared including a zirconia powder (precursor powder 1) including alumina by a content of 0.05% by mass and yttria by a content of 2.5 mol %. In the obtained zirconia powder (precursor powder 1), the BET specific surface area was 9.1 m$^2$/g.

By using a method similar to the method of preparing the precursor powder 2 of Example 1 except that yttria was mixed to adjust the yttria content to 8.5 mol %, a slurry was prepared including a zirconia powder (precursor powder 2) including alumina by a content of 0.05% by mass and yttria by a content of 8.5 mol %. In the obtained zirconia powder, the BET specific surface area was 11.3 m$^2$/g.

The difference in the yttria content between the yttria content for the slurry of the precursor powder 1 and that for the slurry of the precursor powder 2 was 6.0 mol %. The slurries were mixed to adjust the yttria content to 5.5 mol %, and then the obtained mixture was dried to obtain a zirconia powder including alumina by a content of 0.05% by mass and yttria by a content of 5.5 mol %.

The obtained zirconia powder was molded, pre-sintered, and sintered by a method similar to the method of Example 1 except that the zirconia powder obtained by the method according to the present Example was used to obtain a zirconia sintered body of the present Example.

Example 7

By using a method similar to the method of preparing the precursor powder 1 of Example 1 except that yttria was mixed to adjust the yttria content to 2.5 mol % and that the zirconia powder was treated by heat treatment at 1,160° C. for 2 hours in the atmosphere, a slurry was prepared including a zirconia powder (precursor powder 1) including alumina by a content of 0.05% by mass and yttria by a content of 2.5 mol %. In the obtained zirconia powder, the BET specific surface area was 10.0 $m^2/g$.

By using a method similar to the method of preparing the precursor powder 2 of Example 1 except that yttria was mixed to adjust the yttria content to 8.5 mol %, a slurry was prepared including a zirconia powder (precursor powder 2) including alumina by a content of 0.05% by mass and yttria by a content of 8.5 mol %. In the obtained zirconia powder, the BET specific surface area was 11.3 $m^2/g$.

The difference in the yttria content between the yttria content for the slurry of the precursor powder 1 and that for the slurry of the precursor powder 2 was 6.0 mol %. The slurries were mixed to adjust the yttria content to 5.5 mol %, and then the obtained mixture was dried to obtain a zirconia powder including alumina by a content of 0.05% by mass and yttria by a content of 5.5 mol %.

The obtained zirconia powder was molded, pre-sintered, and sintered by a method similar to the method of Example 1 except that the zirconia powder obtained by the method according to the present Example was used to obtain a zirconia sintered body of the present Example.

Example 8

By using a method similar to the method of preparing the precursor powder 1 of Example 1 except that yttria was mixed to adjust the yttria content to 1.5 mol % and that the zirconia powder was treated by heat treatment at 1,150° C. for 2 hours in the atmosphere, a slurry was prepared including a zirconia powder (precursor powder 1) including alumina by a content of 0.05% by mass and yttria by a content of 1.5 mol %. In the obtained zirconia powder, the T+C phase ratio was 0%, and the BET specific surface area was 10.7 $m^2/g$. In addition, a slurry was obtained including the precursor powder 2 by a method similar to the method of Example 4.

The difference in the yttria content between the yttria content for the slurry of the precursor powder 1 and that for the slurry of the precursor powder 2 was 4.0 mol %. The slurries were mixed to adjust the yttria content to 4.8 mol %, and then the obtained mixture was dried to obtain a zirconia powder including alumina by a content of 0.05% by mass and yttria by a content of 4.8 mol %.

The obtained zirconia powder was molded, pre-sintered, and sintered by a method similar to the method of Example 1 except that the zirconia powder obtained by the method according to the present Example was used to obtain a zirconia sintered body of the present Example.

Example 9

A method similar to the method of Example 8 except that the slurry of the precursor powder 1 and the slurry of the precursor powder 2 were mixed to adjust the yttria content to 5.0 mol % was performed to obtain a zirconia powder including alumina by a content of 0.05% by mass and yttria by a content of 5.0 mol %.

The obtained zirconia powder was molded, pre-sintered, and sintered by a method similar to the method of Example 1 except that the zirconia powder obtained by the method according to the present Example was used to obtain a zirconia sintered body of the present Example.

Example 10

A method similar to the method of Example 1 was performed except that the slurry of the precursor powder 1 and the slurry of the precursor powder 2 were mixed to adjust the yttria content to 5.8 mol % to obtain a zirconia powder including alumina by a content of 0.05% by mass and yttria by a content of 5.8 mol %.

The obtained zirconia powder was molded, pre-sintered, and sintered by a method similar to the method of Example 1 except that the zirconia powder obtained by the method according to the present Example was used to obtain a zirconia sintered body of the present Example.

Example 11

A method similar to the method of Example 1 was performed except that the obtained zirconia powder was treated by heat treatment at 1,140° C. for 2 hours in the atmosphere and that alumina was not used, a slurry was prepared including a zirconia powder (precursor powder 1) including yttria by a content of 2.5 mol %. In the obtained zirconia powder (precursor powder 1), the T+C phase ratio was 17% and the BET specific surface area was 11.1 $m^2/g$.

A method similar to the method of preparing the precursor powder 2 of Example 1 was performed to obtain a slurry including a zirconia powder (precursor powder 2) including alumina by a content of 0.05% by mass and yttria by a content of 8.5 mol %.

By using a method similar to the method of Example 1, the slurry of the precursor powder 1 and the slurry of the precursor powder 2 were mixed to obtain a zirconia powder including alumina by a content of 0.023% by mass and yttria by a content of 5.2 mol %.

The obtained zirconia powder was molded, pre-sintered, and sintered by a method similar to the method of Example 1 except that the zirconia powder obtained by the method according to the present Example was used to obtain a zirconia sintered body of the present Example.

Example 12

A method similar to the method of preparing the precursor powder 1 of Example 1 except that yttria was mixed to adjust the yttria content to 2.0 mol %, that the obtained zirconia powder was treated by heat treatment at 1,160° C. for 2 hours in the atmosphere, and that alumina was not used, a slurry was prepared including a zirconia powder (precursor powder 1) including yttria by a content of 2.0 mol %. In the obtained zirconia powder (precursor powder 1), the T+C phase ratio was 5% and the BET specific surface area was 10.2 m²/g.

A method similar to the method of preparing the precursor powder 2 of Example 1 except that the obtained zirconia powder was treated by heat treatment at 1,130° C. for 2 hours in the atmosphere and that alumina was not used, a slurry was prepared including a zirconia powder (precursor powder 2) including yttria by a content of 8.5 mol %. In the obtained zirconia powder (precursor powder 2), the BET specific surface area was 12.4 m²/g.

The difference in the yttria content between the yttria content for the slurry of the precursor powder 1 and that for the slurry of the precursor powder 2 was 6.5 mol %. By using a method similar to the method of Example 1, the slurry of the precursor powder 1 and the slurry of the precursor powder 2 were mixed to obtain a zirconia powder not including alumina (including alumna by a content of 0% by mass) and including yttria by a content of 5.2 mol %.

The obtained zirconia powder was molded, pre-sintered, and sintered by a method similar to the method of Example 1 except that the zirconia powder obtained by the method according to the present Example was used to obtain a zirconia sintered body of the present Example.

Comparative Example 1

By using a method similar to the method of preparing the precursor powder 1 of Example 1 except that yttria was mixed to adjust the yttria content to 2.0 mol %, a slurry was prepared including a zirconia powder (precursor powder 1) including alumina by a content of 0.05% by mass and yttria by a content of 2.0 mol %. In the obtained zirconia powder, the T+C phase ratio was 5%, the average crystallite size was 205 Å, and the BET specific surface area was 13.6 m²/g.

By using a method similar to the method of preparing the precursor powder 2 of Example 1 except that yttria was mixed to adjust the yttria content to 5.5 mol %, a slurry was prepared including a zirconia powder (precursor powder 2) including alumina by a content of 0.05% by mass and yttria by a content of 5.5 mol %. In the obtained zirconia powder, the T+C phase ratio was 97%, the average crystallite size was 340 Å, and the BET specific surface area was 10.0 m²/g.

The difference in the yttria content between the yttria content for the slurry of the precursor powder 1 and that for the slurry of the precursor powder 2 was 3.5 mol %. The slurries were mixed to adjust the yttria content to 5.2 mol %, and then the obtained mixture was dried to obtain a zirconia powder including alumina by a content of 0.05% by mass and yttria by a content of 5.2 mol %.

The obtained zirconia powder was molded, pre-sintered, and sintered by a method similar to the method of Example 1 except that the zirconia powder obtained by the method according to the present Comparative example was used to obtain a zirconia sintered body of the present Comparative example.

Comparative Example 2

By using a method similar to the method of preparing the precursor powder 1 of Example 1 except that yttria was mixed to adjust the yttria content to 3.0 mol %, a slurry was prepared including a zirconia powder (precursor powder 1) including alumina by a content of 0.05% by mass and yttria by a content of 3.0 mol %. In the obtained zirconia powder, the T+C phase ratio was 42%, the average crystallite size was 236 Å, and the BET specific surface area was 9.5 m²/g.

By using a method similar to the method of preparing the precursor powder 2 of Example 1 except that yttria was mixed to adjust the yttria content to 5.5 mol %, a slurry was prepared including a zirconia powder (precursor powder 2) including alumina by a content of 0.05% by mass and yttria by a content of 5.5 mol %. In the obtained zirconia powder, the T+C phase ratio was 97%, the average crystallite size was 340 Å, and the BET specific surface area was 10.0 m²/g.

The difference in the yttria content between the yttria content for the slurry of the precursor powder 1 and that for the slurry of the precursor powder 2 was 2.5 mol %. The slurries were mixed to adjust the yttria content to 5.2 mol %, and then the obtained mixture was dried to obtain a zirconia powder including alumina by a content of 0.05% by mass and yttria by a content of 5.2 mol %.

The obtained zirconia powder was molded, pre-sintered, and sintered by a method similar to the method of Example 1 except that the zirconia powder obtained by the method according to the present Comparative example was used to obtain a zirconia sintered body of the present Comparative example.

Comparative Example 3

By using a method similar to the method of preparing the precursor powder 1 of Example 1 except that yttria was mixed to adjust the yttria content to 5.2 mol %, a slurry was prepared including a zirconia powder including alumina by a content of 0.05% by mass and yttria by a content of 5.2 mol %.

The obtained slurry was dried to obtain a zirconia powder including alumina by a content of 0.05% by mass and yttria by a content of 5.2 mol %.

The obtained zirconia powder was molded, pre-sintered, and sintered by a method similar to the method of Example 1 except that the zirconia powder obtained by the method according to the present Comparative example was used to obtain a zirconia sintered body of the present Comparative example. In the obtained pre-sintered body, the maximum frequency was 30% and the difference between the highest value and the lowest value for the yttrium concentration was 2.2 mol %.

Comparative Example 4

By using a method similar to the method of preparing the precursor powder 1 of Example 1 except that yttria was mixed to adjust the yttria content to 5.5 mol %, a slurry was prepared including a zirconia powder including alumina by a content of 0.05% by mass and yttria by a content of 5.5 mol %.

The obtained slurry was dried to obtain a zirconia powder including alumina by a content of 0.05% by mass and yttria by a content of 5.5 mol %.

The obtained zirconia powder was molded, pre-sintered, and sintered by a method similar to the method of Example 1 except that the zirconia powder obtained by the method according to the present Comparative example was used to obtain a zirconia sintered body of the present Comparative example.

Comparative Example 5

A method compliant with Example 14 of Patent Literature 2 was performed to obtain a zirconia sintered body. Specifically, by using a method similar to the method used to prepare the precursor powder 1 of Example 1 except that yttria was mixed to adjust the yttria content to 3.0 mol %, a slurry was prepared including a zirconia powder (precursor powder 1) including alumina by a content of 0.05% by mass and yttria by a content of 3.0 mol %. In the obtained zirconia powder, the BET specific surface area was 13.0 m²/g.

In addition, by using a method similar to the method of preparing the precursor powder 2 of Example 1 except that yttria was mixed to adjust the yttria content to 5.5 mol %, a slurry was prepared including a zirconia powder (precursor powder 2) including alumina by a content of 0.05% by mass and yttria by a content of 5.5 mol %. In the obtained zirconia powder, the T+C phase ratio was 97%, the average crystallite size was 340 Å, and the BET specific surface area was 10.0 m²/g.

The difference in the yttria content between the yttria content for the slurry of the precursor powder 1 and that for the slurry of the precursor powder 2 was 2.5 mol %. The slurries were mixed to adjust the yttria content to 4.5 mol %, and then the obtained mixture was dried to obtain a zirconia powder including alumina by a content of 0.05% by mass and yttria by a content of 4.5 mol %.

The obtained zirconia powder was molded, pre-sintered, and sintered by a method similar to the method of Example 1 except that the zirconia powder obtained by the method according to the present Comparative example was used to obtain a zirconia sintered body of the present Comparative example.

Comparative Example 6

A method compliant with Example 40 of Patent Literature 3 was performed to obtain a green body. Specifically, commercial zirconia powders containing yttria by a content of 3.0 mol % and by a content of 6.0 mol %, respectively, were mixed to obtain a powder including zirconia including yttria by a content of 4.2 mol %.

A method similar to the method of Example 1 except that the zirconia powder obtained by the method according to the present Comparative example was used and that the sintering temperature was 1,500° C. was performed to obtain a zirconia sintered body of the present Comparative example.

Comparative Example 7

A method compliant with Example 42 of Patent Literature 3 was performed to obtain a green body. Specifically, commercial zirconia powders containing yttria by a content of 4.0 mol %, 5.0 mol %, and 6.0 mol %, respectively, an alumina powder, and a magnesia powder were mixed to obtain a powder including zirconia including alumina by a content of 0.2% by mass and magnesia by 0.2% by mass, and yttria by a content of 5.5 mol % as the remainder.

A method similar to the method of Comparative example 6 except that the powder obtained by the method of the present Comparative example was used was performed to obtain a zirconia sintered body of the present Comparative example.

Evaluation results for the zirconia sintered bodies of the Examples and the Comparative examples will be shown in Table 1 below and those for the zirconia sintered bodies will be shown in Table 2 below.

TABLE 1

| | $Y_2O_3$ (mol %) | $Al_2O_3$ (wt %) | BET specific surface area (m²/g) | T + C phase ratio (%) | Average crystallite size (Å) |
|---|---|---|---|---|---|
| Example 1 | 5.2 | 0.05 | 10.6 | 58 | 375 |
| Example 2 | 5.2 | 0.05 | 9.8 | 77 | 355 |
| Example 3 | 5.2 | 0.05 | 9.7 | 59 | 396 |
| Example 4 | 5.2 | 0.05 | 10.1 | 90 | 338 |
| Example 5 | 5.2 | 0.05 | 10.0 | 84 | 332 |
| Example 6 | 5.5 | 0.05 | 10.2 | 65 | 377 |
| Example 7 | 5.5 | 0.05 | 10.7 | 63 | 379 |
| Example 8 | 4.8 | 0.05 | 10.1 | — | — |
| Example 9 | 5.0 | 0.05 | 10.1 | — | — |
| Example 10 | 5.8 | 0.05 | 10.7 | — | — |
| Example 11 | 5.2 | 0.023 | 11.2 | — | — |
| Example 12 | 5.2 | 0 | 11.3 | — | — |
| Comparative example 1 | 5.2 | 0.05 | 10.3 | 91 | 344 |
| Comparative example 2 | 5.2 | 0.05 | 9.9 | 89 | 321 |
| Comparative example 3 | 5.2 | 0.05 | 9.3 | 98 | 327 |
| Comparative example 4 | 5.5 | 0.05 | 10.0 | 97 | 340 |
| Comparative example 5 | 4.5 | 0.05 | 10.0 | 77 | 303 |
| Comparative example 6 | 4.2 | 0 | 7.1 | 76 | 280 |
| Comparative example 7 | 5.5 | 0.2 | 6.9 | 87 | 314 |

Note:
In Table 1, the dash indicates "Not measured".

TABLE 2

| | Average crystal grain size (μm) | Relative density (%) | Translucency (%) | Parallel light transmittance (%) | PT/TT ratio | Three-point bending strength (MPa) |
|---|---|---|---|---|---|---|
| Example 1 | 0.77 | 99.93 | 50.1 | 0.7 | 0.7 | 831 |
| Example 2 | 0.79 | 99.90 | 49.4 | 0.7 | 0.5 | 861 |
| Example 3 | 0.56 | 99.90 | 47.4 | 0.6 | 0.5 | 845 |
| Example 4 | 0.69 | 99.90 | 51.4 | 0.8 | 1.2 | 807 |
| Example 5 | 0.80 | 99.87 | 50.3 | 0.7 | 0.8 | 717 |
| Example 6 | — | 99.92 | 50.3 | 0.7 | 0.5 | 728 |
| Example 7 | — | 99.95 | 51.0 | 0.7 | 0.6 | 769 |
| Example 8 | — | 99.93 | 49.2 | 0.6 | 0.6 | 961 |
| Example 9 | — | 99.95 | 49.9 | 0.6 | 0.7 | 843 |
| Example 10 | — | 99.81 | 50.8 | 0.8 | 1.3 | 704 |
| Example 11 | — | 99.95 | 49.2 | 0.6 | 0.6 | 711 |
| Example 12 | — | 99.95 | 48.4 | 0.6 | 0.5 | 753 |
| Comparative example 1 | 0.75 | 99.92 | 50.9 | 0.8 | 1.4 | 654 |
| Comparative example 2 | — | 99.87 | 48.3 | — | — | 662 |
| Comparative example 3 | 0.73 | 99.93 | 50.7 | 0.8 | 1.8 | 664 |
| Comparative example 4 | 0.77 | 99.95 | 52.2 | 0.8 | 1.2 | 635 |
| Comparative example 5 | — | 99.84 | 46.2 | — | — | 815 |
| Comparative example 6 | — | — | 43.0 | — | — | 804 |
| Comparative example 7 | — | — | 24.8 | — | — | 500 |

Note:
In Table 2, the dash indicates "Not measured".

It is verified based on the above Examples and Comparative examples that a zirconia sintered body with the light transmittance higher than 47%, the PT/TT ratio of 1.0 or less, and the three-point bending strength higher than 700 MPa can be obtained from the zirconia powder according to any of the above Examples even if the sintering is implemented by normal-pressure sintering in an air atmosphere.

On the contrary, it is verified that if either of the T+C phase ratio or the average crystallite size is outside the range of the present embodiment, the three-point bending strength becomes low and further the transparency becomes high. Further, it is verified based on Comparative examples 1 and 2 that no zirconia sintered body of the present embodiment may be obtained if precursor powders of different yttria contents are merely mixed. Moreover, it is verified that no zirconia sintered body of the present embodiment may be obtained because the translucency may become insufficient if the yttria content is low and if precursor powders of different yttria contents are merely mixed. Further, referring to Comparative examples 6 and 7, in which sintered bodies of examples of Patent Literature 3 were imparted with a high translucency by performing sintering in an oxygen atmosphere, it is verified that the light transmittance is lower compared to the light transmittance in Examples of the present embodiment.

In addition, it is verified that in any of Comparative examples 3 to 4 obtained from a single zirconia powder, the three-point bending strength becomes lower than 700 MPa.

FIG. 1 illustrates an SEM image of a surface of the zirconia sintered body of Example 1 of the present embodiment. It is verified that the zirconia sintered body of Example 1 includes coarse crystal grains with the longer sizes ranging from 1.0 to 1.7 μm and fine crystal grains with the longer sizes ranging from 0.1 to 0.4 μm. As indicated by the portions of FIG. 1 respectively highlighted with a circle, it is verified that the zirconia sintered body illustrated in FIG. 1 includes a structure including a grain boundary formed between multiple fine crystal grains and a coarse crystal grain.

FIG. 2 is a graph illustrating a relationship between the number ratio of crystal grains with the yttria concentration ranging from 3 to 4 mol % to the entire crystal grains and the three-point bending strength. Referring to FIG. 2, it is verified that the three-point bending strength becomes 700 MPa or higher when the ratio becomes 10% or higher and that the three-point bending strength becomes 820 MPa or higher when the ratio becomes 25% or higher Moreover, in Comparative example 3 in which the zirconia sintered body was obtained from a single zirconia powder, the difference of concentration among crystal grains was 2.65 mol %, a level lower than 3 mol %, while in the zirconia sintered bodies of Examples 1 to 4 in which the three-point bending strength is 800 MPa or higher, the difference of concentration among crystal grains was 3.55 mol %, 4.17 mol %, 4.77 mol %, and 3.24 mol %, i.e., a level higher than 3 mol %, respectively. In addition, in the zirconia sintered body obtained by sintering a zirconia powder obtained by a method similar to the method of Example 1 at 1,550° C., the difference of the concentration among crystal grains was 3.14 mol %. It was verified from this result that in the zirconia powder of Example 1, the difference of concentration among crystal grains becomes small due to the sintering temperature set at a high temperature.

Furthermore, in typical Examples and Comparative examples, the monoclinic crystal frequency was measured for samples measured for the three-point bending strength. Table 3 below shows the results of the measurement.

TABLE 3

|  | Monoclinic crystal frequency (%) | Three-point bending strength (MPa) |
|---|---|---|
| Example 1 | 54 | 831 |
| Example 3 | 73 | 845 |
| Example 4 | 53 | 807 |
| Comparative example 3 | 35 | 664 |

It is known from the above results that in any of the Examples in which the three-point bending strength was 800 MPa or higher, the monoclinic crystal frequency was 40% or higher, and it is verified that the three-point bending strength tends to be higher if the monoclinic crystal frequency becomes higher.

Example 13

A method similar to the method of Example 1 except that a zirconia powder obtained by a method similar to the method of Example 2 was used and that the sintering temperature was 1,550° C. was performed to obtain a zirconia sintered body of the present Example.

Example 14

A method similar to the method of Example 13 except that a zirconia powder obtained by a method similar to the method of Example 4 was used was performed to obtain a zirconia sintered body of the present Example.

Example 15

A method similar to the method of Example 13 except that a zirconia powder obtained by a method similar to the method of Example 5 was used was performed to obtain a zirconia sintered body of the present Example.

Example 16

A method similar to the method of Example 13 except that a zirconia powder obtained by a method similar to the method of Example 8 was used was performed to obtain a zirconia sintered body of the present Example.

Example 17

A method similar to the method of Example 13 except that a zirconia powder obtained by a method similar to the method of Example 9 was used was performed to obtain a zirconia sintered body of the present Example.

Comparative Example 8

A method similar to the method of Example 13 except that a zirconia powder obtained by a method similar to the method of Comparative example 1 was used was performed to obtain a zirconia sintered body of the present Comparative example.

Comparative Example 9

A method similar to the method of Example 13 except that a zirconia powder obtained by a method similar to the method of Comparative example 2 was used was performed to obtain a zirconia sintered body of the present Comparative example.

Comparative Example 10

A method similar to the method of Example 13 except that a zirconia powder obtained by a method similar to the method of Comparative example 3 was used was performed to obtain a zirconia sintered body of the present Comparative example.

Results thereof will be shown in Table 4 below.

TABLE 4

|  | Average crystal grain size (μm) | Relative density (%) | Translucency (%) | Parallel light transmittance (%) | PT/TT ratio | Three-point bending strength (MPa) |
|---|---|---|---|---|---|---|
| Example 13 | 1.57 | 99.88 | 48.7 | 0.6 | 0.4 | 716 |
| Example 14 | 1.51 | 99.90 | 52.1 | 0.7 | 0.6 | 736 |
| Example 15 | 1.61 | 99.88 | 48.6 | 0.6 | 0.5 | 726 |
| Example 16 | — | 99.90 | 49.2 | 0.6 | 0.5 | 732 |
| Example 17 | — | 99.92 | 49.2 | 0.6 | 0.4 | 770 |
| Comparative example 8 | 1.62 | 99.90 | 50.1 | 0.6 | 0.6 | 643 |
| Comparative example 9 | — | 99.88 | 49.0 | — | — | 646 |
| Comparative example 10 | 1.59 | 99.90 | 52.1 | 0.7 | 0.8 | 598 |

Note:
In Table 4, the dash indicates "Not measured".

It is verified based on comparison between Comparative examples 3 and 10 that in zirconia powder of prior art, the average crystal grain size increased due to the rise of the sintering temperature and that the light transmittance improved in accordance with the increase in the average crystal grain size. On the contrary, in the zirconia sintered body of the Examples, it is verified that the light transmittance tends to be lower even when the average crystal grain size increases due to the rise in the sintering temperature. As described above, it is verified that for the zirconia powder according to the present embodiment, a zirconia sintered body with the translucency and the mechanical strength higher for the process of using normal-pressure sintering at the sintering temperature of 1,450° C. compared with the process of using normal-pressure sintering at the sintering temperature of 1,550° C. can be obtained.

All of the Description, Claims, Drawings, and Abstract of Japanese Patent Application No. 2019-185075 filed on Oct. 8, 2019 are cited and incorporated herein by reference in their entirety as a disclosure disclosed in the Description of the present disclosure.

The invention claimed is:

1. A zirconia sintered body comprising yttria and zirconia, including yttria by a content ranging from 4.5 mol % or more to 6.5 mol % or less and zirconia as the remainder, the total light transmittance of a 1-mm thick sample measured in compliance with JIS K 7361-1 being 46.5% or higher, the three-point bending strength being 700 MPa or higher, and a ratio of an integrated value for total light transmittance to an integrated value for parallel light transmittance of a 1-mm thick sample measured at measurement wavelength ranging from 400 to 700 nm being 1.3% or less,
wherein a difference in the yttria concentration between a crystal grain with the highest yttria concentration and a crystal grain with the lowest yttria concentration is 2.7 mol % or higher and 7 mol % or less.

2. The zirconia sintered body according to claim 1 comprising alumina.

3. The zirconia sintered body according to claim 2, wherein the content of alumina is 0.005% by mass or higher and 0.2% by mass or less.

4. The zirconia sintered body according to claim 1, wherein an average crystal grain size is in a range of 0.5 μm or greater and 1.8 μm or less.

5. The zirconia sintered body according to claim 1, wherein a difference in the yttria concentration between a crystal grain with the highest yttria concentration and a crystal grain with the lowest yttria concentration is 3.2 mol % or higher and 5 mol % or less.

6. The zirconia sintered body according to claim 1, wherein a number ratio of crystal grains with a yttria concentration ranging from 3.0 mol % or higher to 4.0 mol % or less to all the crystal grains is 10% or higher and 50% or less.

7. A production method of the zirconia sintered body according to claim 1, the production method comprising a process of sintering a green body including a zirconia powder which includes a yttria source and zirconia, wherein the content of the yttria source is 4.5 mol % or more and 6.5 mol % or less and the remainder is zirconia, a total ratio of tetragonal and cubic crystals to the entire crystal phase of zirconia is 90% or less, a Brunauer, Emmett and Teller (BET) specific surface area is 7.5 $m^2/g$ or more and 15 $m^2/g$ or less, and an average crystallite size is 325 Å or greater.

8. The production method according to claim 7, wherein a difference between the yttria content of one zirconia powder particle and the yttria content of the other zirconia powder particle is greater than 3.0 mol %.

9. The production method according to claim 7, wherein the sintering in the process is normal pressure sintering.

* * * * *